United States Patent [19]

Sircom

[11] Patent Number: 5,662,610

[45] Date of Patent: Sep. 2, 1997

[54] AUTOMATIC NEEDLE GUARD TIP PROTECTION

[76] Inventor: Richard C. Sircom, 19 Richards Drive, Dartmouth, N.S., Canada, B3A 2P1

[21] Appl. No.: 488,294

[22] Filed: Jun. 7, 1995

Related U.S. Application Data

[63] Continuation-in-part of Ser. No. 272,598, Jul. 11, 1994, Pat. No. 5,611,781, which is a continuation of Ser. No. 672,651, Mar. 20, 1991, Pat. No. 5,328,482, which is a continuation-in-part of Ser. No. 309,305, Feb. 1, 1989, Pat. No. 4,921,517.

[51] Int. Cl.⁶ ..................................................... A61M 5/32
[52] U.S. Cl. ........................... 604/110; 604/198; 604/263
[58] Field of Search ................................... 604/110, 272, 604/263, 164, 198, 163, 192

[56] References Cited

U.S. PATENT DOCUMENTS 5,322,517  6/1994  Sircom et al. ........................ 604/198

*Primary Examiner*—John D. Yasko

[57] ABSTRACT

A needle tip protecting device is provided for hypodermic needles, catheters and the like. The device is small enough to be stored at the base of the needle prior to and during use. After use it may be slid to cover the needle tip where it automatically self-attaches and becomes non-removable. Embodiments of mechanisms which achieve this effect by means of a tapered cavity, collet or angled jamming surface are described.

12 Claims, 24 Drawing Sheets

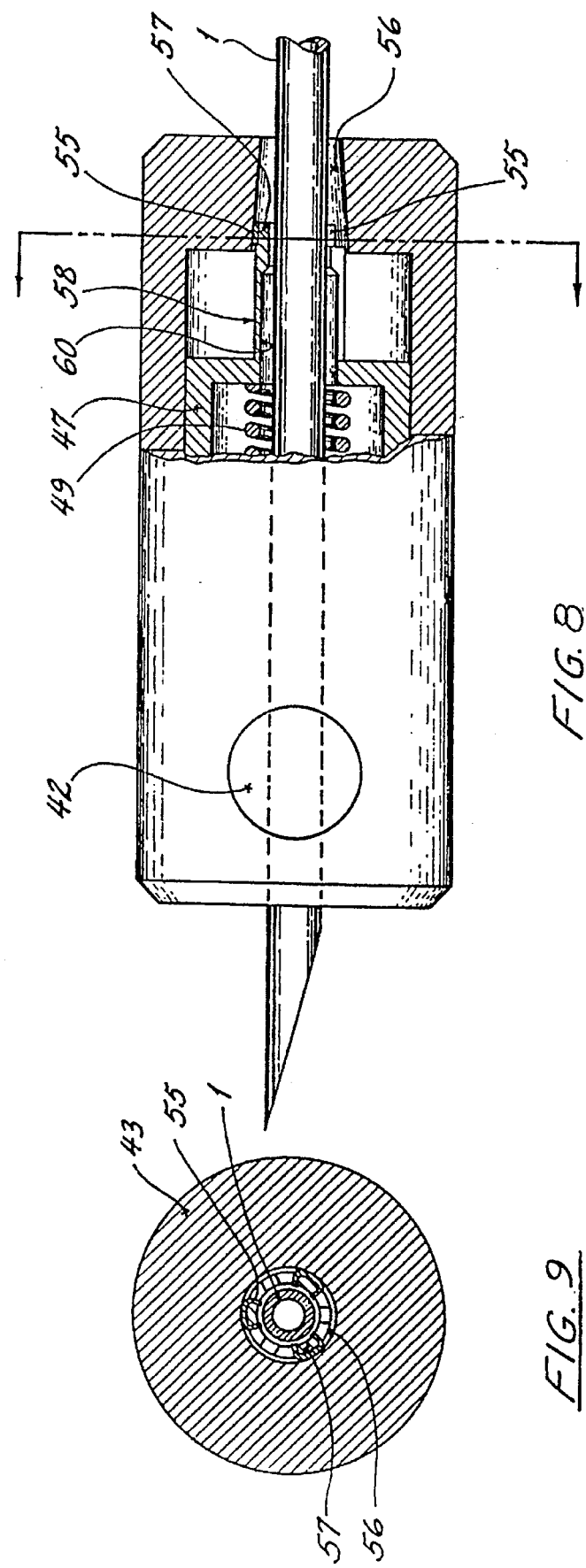

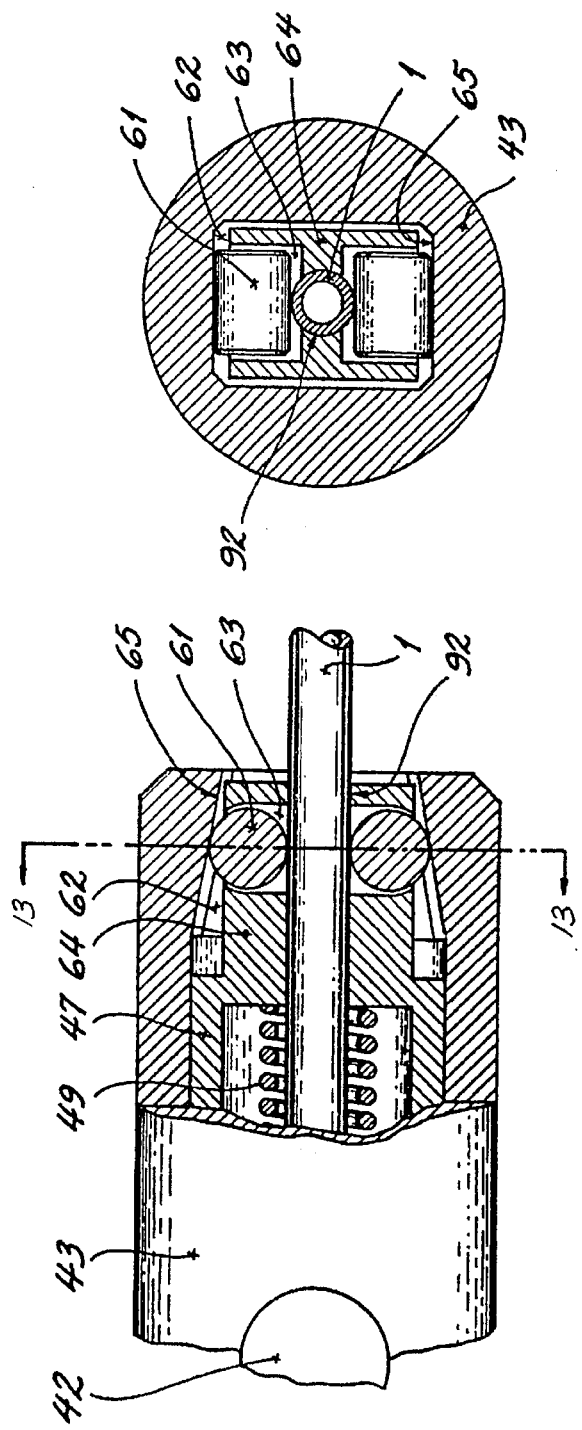
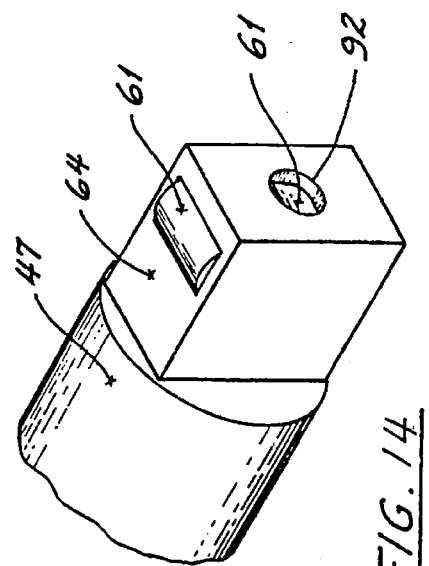
FIG. 12
FIG. 13
FIG. 14

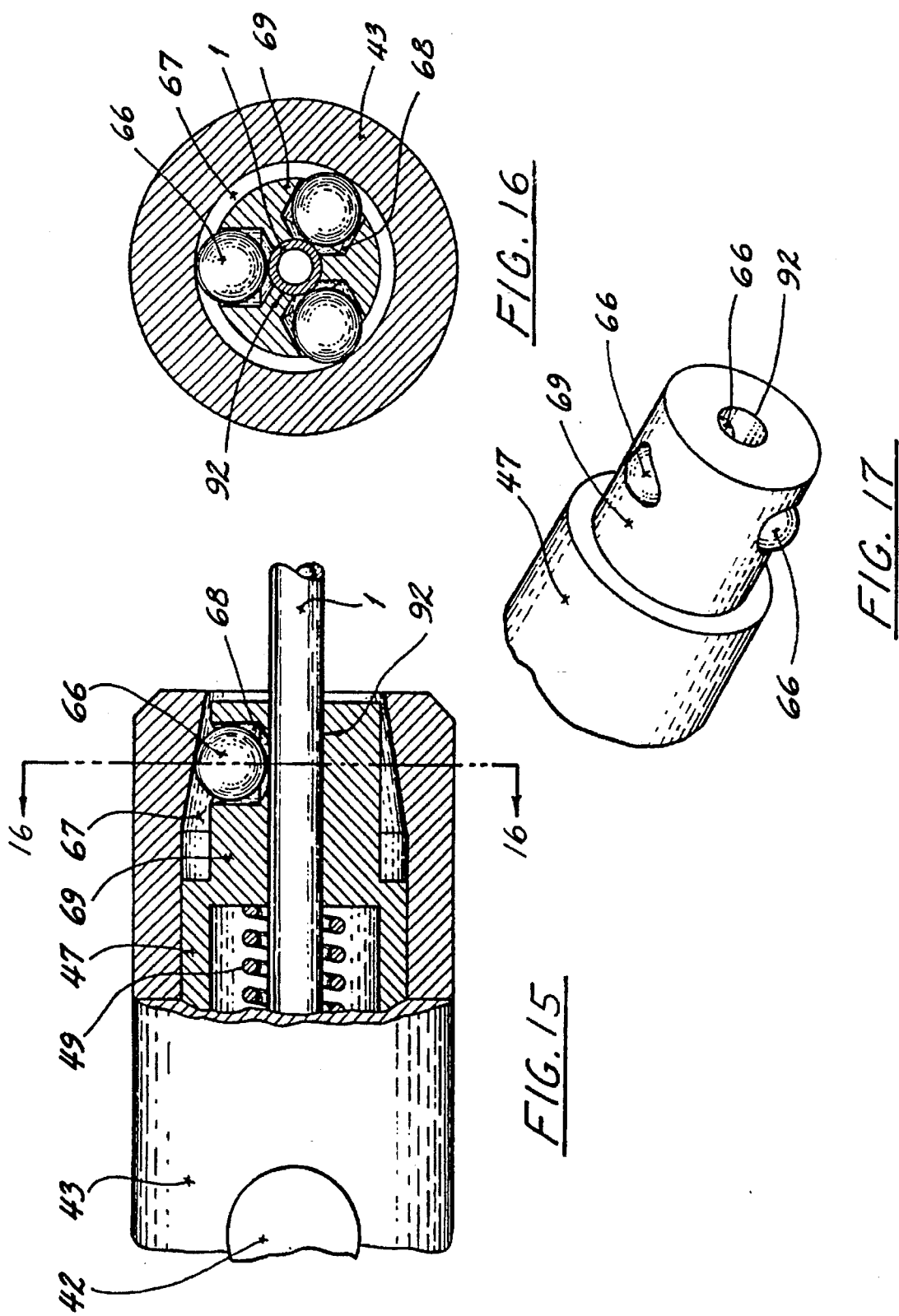

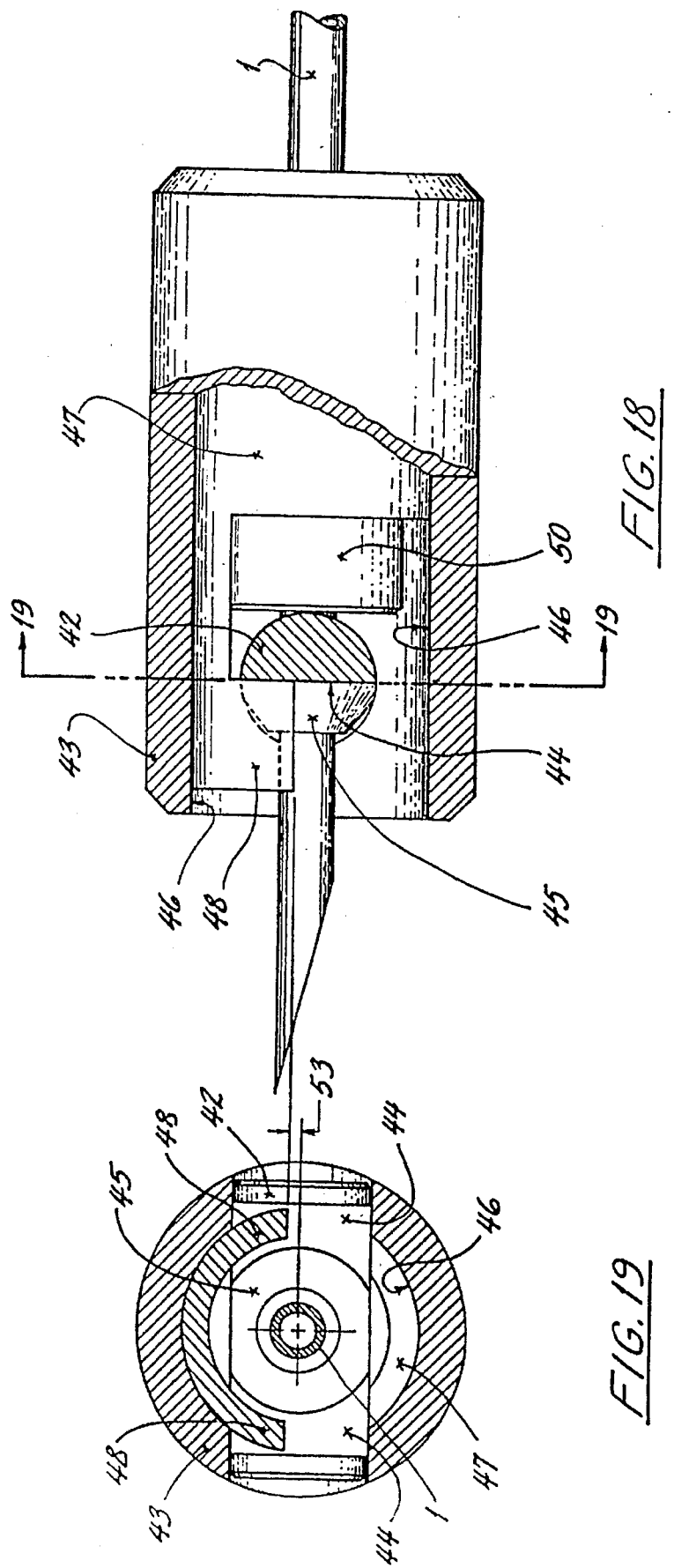

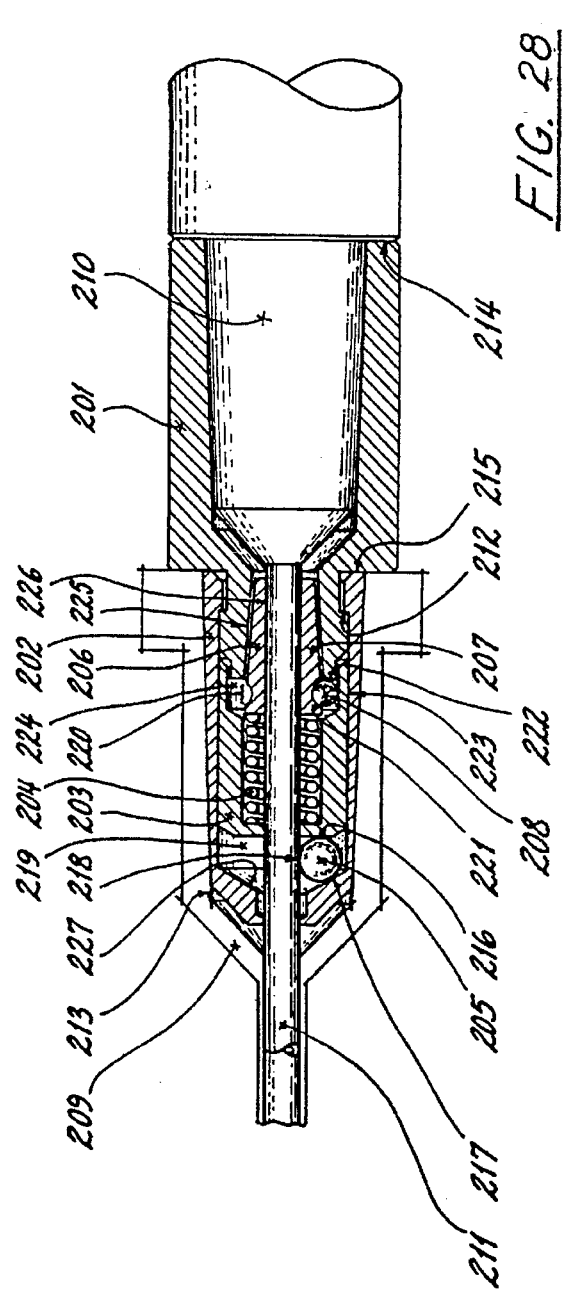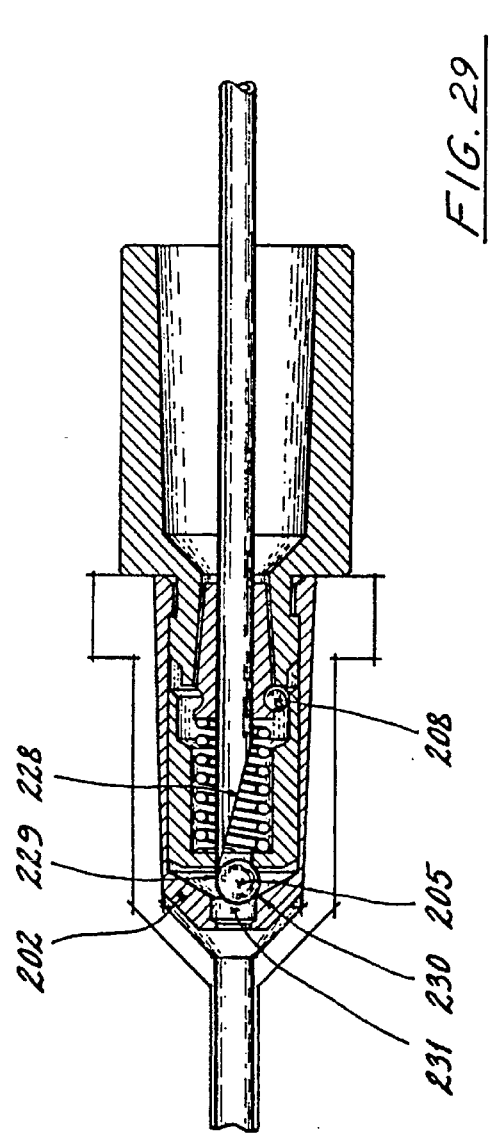

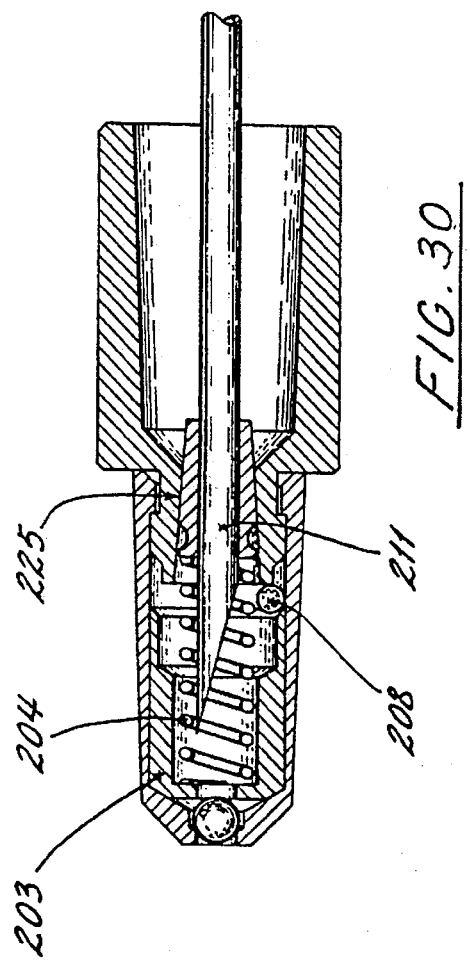
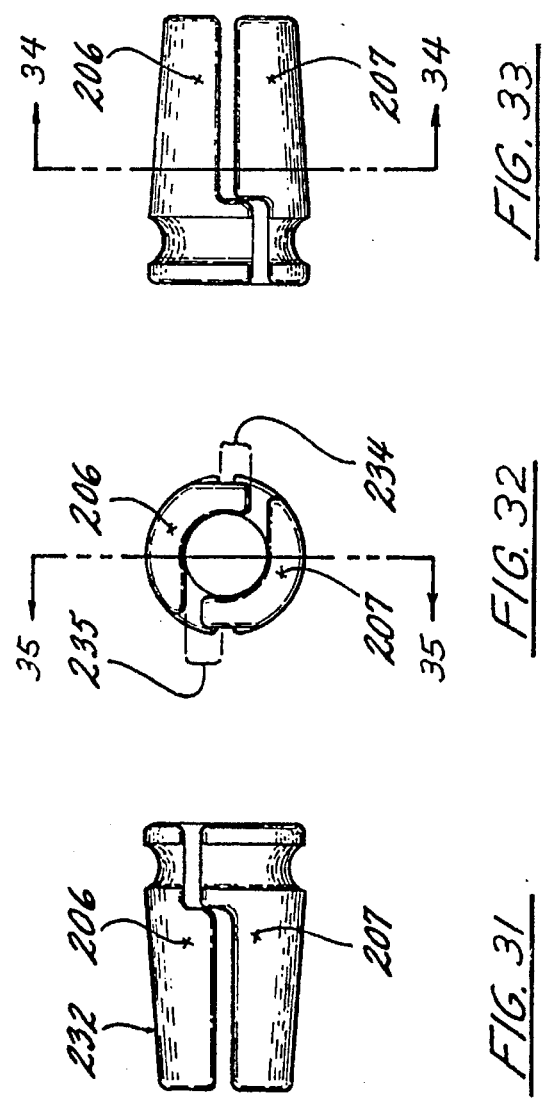

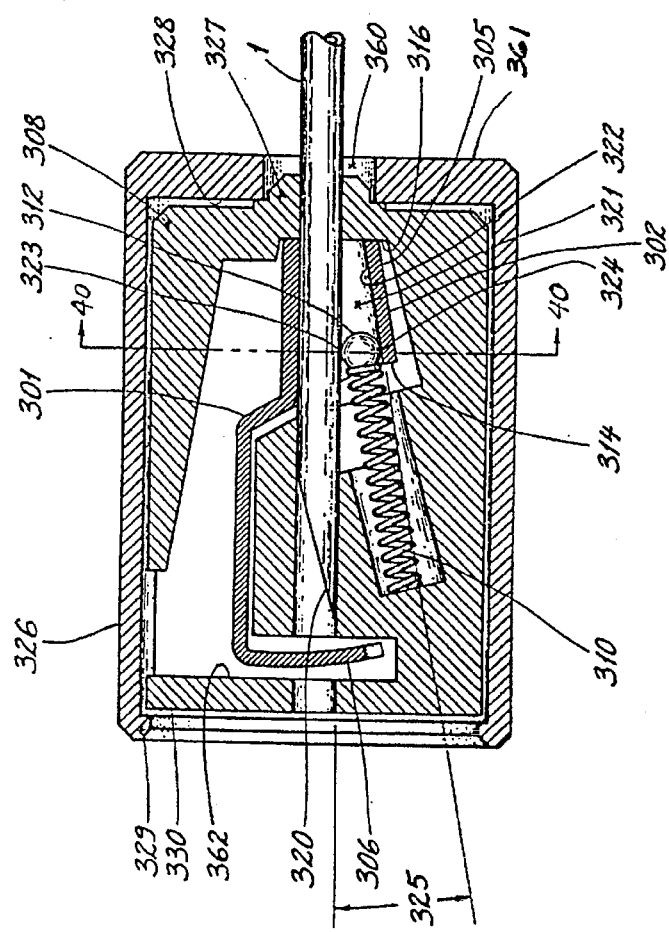
FIG. 39
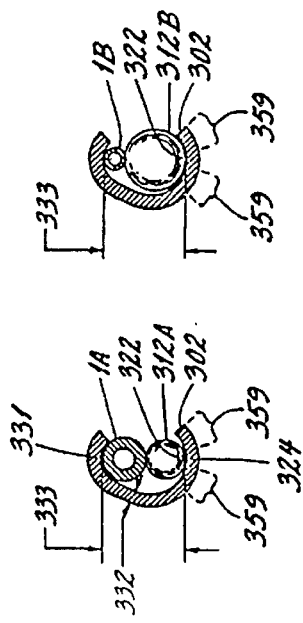
FIG. 41
FIG. 40

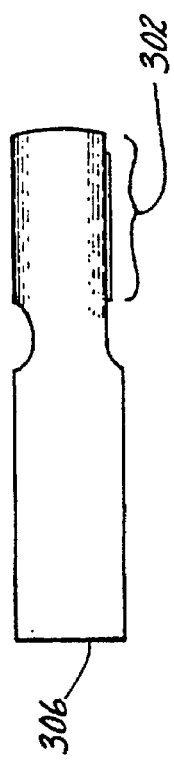
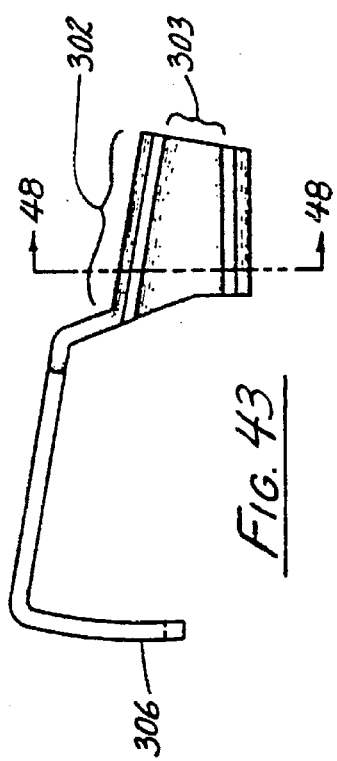
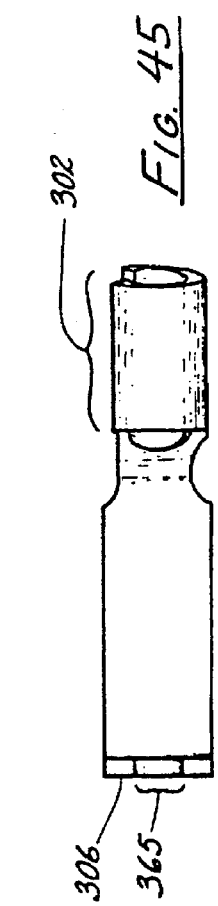
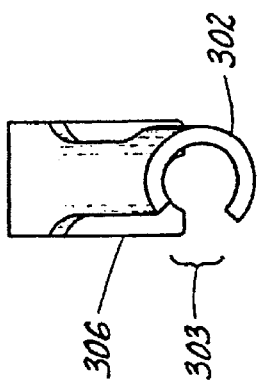
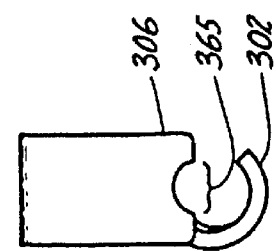

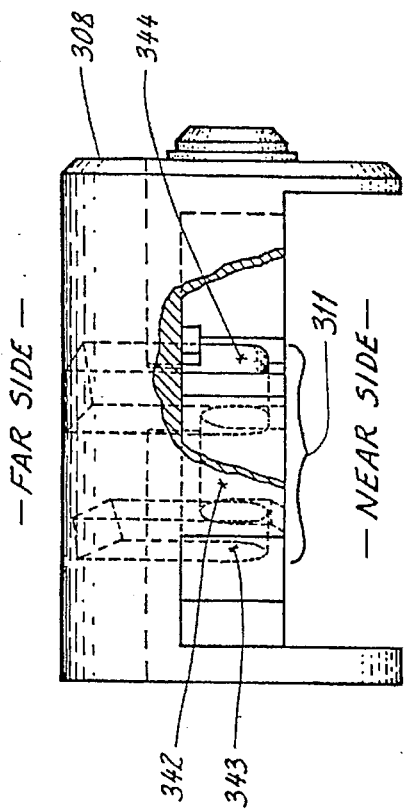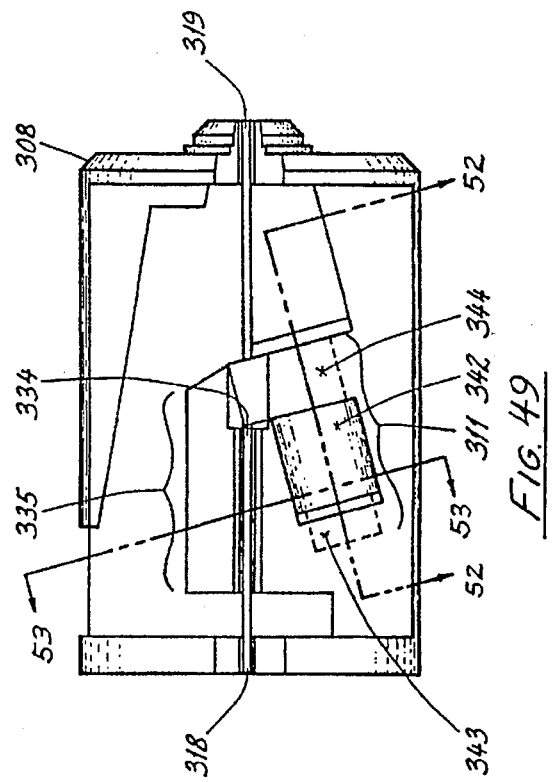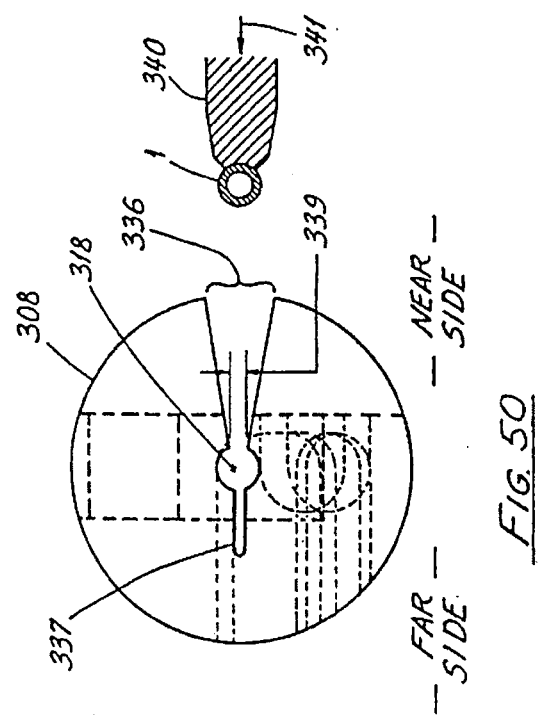

AUTOMATIC NEEDLE GUARD TIP PROTECTION

This application is a CIP of Ser. No. 08/272,598 filed 11 Jul. 1994 now U.S. Pat. No. 5,611,789 which is a continuation of application Ser. No. 07/672,651 filed 20 Mar. 1991 and issued as U.S. Pat. No. 5,328,482 on 12 Jul. 1994, which is a continuation-in-part of Ser. No. 07/309,305 filed 1 Feb. 1989, now U.S. Pat. No. 4,921,517.

FIELD OF THE INVENTION

This invention relates to the safe disposal of hypodermic needles by a guard device which protects the needle tip from exposure after use. More particularly, relates to a tip protector which is storable on needle and which automatically locks over the end of the needle when slid into position by the user.

BACKGROUND OF THE INVENTION

The dangers of infection from accidental contact with the pointed end of used hypodermic needles has log been recognized and is well documented. For example, refer to Jagger, Hunt, Brand-Elnaggar and Pearson, the New England Journal of Medicine, August 1988. In most procedures, the greatest avoidable risk of accidental needle puncture, or "needle-stick", occurs during handling of the used needle, when it is generally inserted into a protective sheath for disposal. This action usually requires moving the hand which holds the sheath towards the pointed tip of the needle, and any inaccuracy in this operation raises the possibility of a puncture. The risk of this is greatly increased if the operator is working Under stress, such as time-pressure or fatigue, or is handicapped by marginal eyesight or unsteady hands.

U.S. Pat. Nos. 5,322,517 and 5,328,482 describe needle guards that are essentially "free floating" in that they are stored at the base of the needle and lock to the needle when deployed from the base to the tip of the needle to occupy a covering protective position.

The protective guard preferably is stored prior to use at the base of the needle. In this position it may further be contained within the usual protective sheath which covers a needle prior to use, and may thereby be supplied with the needle in its sealed and sterilized package.

By reason of the fact that the protective guard may be stored on the needle prior to the normal use of the needle, and occupies an insignificant, compact space, its presence produces a minimum interference with the normal use of the needle. In one application the protective guard may be stored adjacent to or even within the enlarged base of a catheter, in an unobtrusive manner that allows the catheter to be inserted in the normal manner.

After withdrawal of the needle following use, the tip of the needle can be immediately covered with the protective guard by a simple manual action of gripping the protective guard with the fingers, sliding it out of its storage position at the base of the needle, and continuing the sliding motion along the needle shaft until the guard just over-reaches the end of the needle. There it automatically locks in position with the tip of the needle safely covered inside the protective guard.

The protective guard may be slid to the needle tip by the direct application of fingers to the guard. Alternately, handle means may be provided either in the form of an arm, or the like, attached to the guard body; or by use of a simple draw string that is initially stored on the protective guard by being wrapped around its exterior casing.

The protective guard achieves its locking effect by being provided with an internal energy storage element, such as a spring, that is capable of initiating a clamping force through a clamping mechanism. This clamping force is applied directly to the exterior surface of the needle shaft. A latching mechanism serves to suspend initiation of the clamping force prior to withdrawal of the needle tip within the protective guard.

A trigger system releases the latching mechanism once the needle tip passes within the protective guard, thereby initiating the clamping force which is applied to the needle, and thereby locking the protective guard in place over the needle tip. These functions occur automatically and enclose the needle tip with a protecting means which is non-removably engaged thereto.

The clamping force need only immobilize the protective guard against axial or longitudinal displacement on the needle. Further, its locking resistance need not be symmetrical. It is essential to have a high locking resistance against further removal of the guard from the needle. In the other direction resistance to the reemergence of the needle tip from the guard can be substituted or supplemented by arranging for an occluding element to occupy the path of the needle and serve as a containment means. Once the tip enters the guard the presence of such a blocking element ensures that the needle tip cannot re-emerge from the guard even where the locking resistance against displacement of the guard towards the needle base is overcome. When such a blocking element is present, it is sufficient for the clamping mechanism to provide only a uni-directional or one-way resistance to further removal of the guard from the needle.

The present invention addresses one of the classes of mechanisms by which a needle guard of such type may engage with a needle.

The invention in its general form will first be described, and then its implementation in terms of specific embodiments will be detailed with reference to the drawings following hereafter. These embodiments are intended to demonstrate the principle of the invention, and the manner of its implementation. The invention in its broadest and more specific forms will then be further described, and defined, in each of the individual claims which conclude this Specification.

SUMMARY OF THE INVENTION

This invention is directed to providing an engagement means for locking the protective guard to a needle based on introducing a jamming element into an angular space, such as may be provided by a tapered cavity or collet. In function it performs similarly to "chuck" systems. The jamming element is forced into locking engagement with the needle by forcing the jamming element between an angled, jamming surface providing a narrowing or tapered gap between the jamming surface and the needle shaft.

In one embodiment of the invention, locking elements or jaws of hardened material may be provided, radially disposed about the needle shaft, and contained within a gradually tapered or narrowing cavity within the body of the guard device which provides an angled surface with respect to the needle and provides a conic chuck arrangement.

In the unlocked state, these jaws may be maintained loosely in the bore but, if small, may be held in a generally uniform distribution about the needle axis by compliant fingers engaging each jaw. These fingers may optionally be constituted by axial extensions of a spring-biased pressure sleeve described further below, which advances the jaws into the narrowing cavity.

From an initial locked state, the pressure sleeve may be released by a trigger mechanism and urged by an energy storage element, such as a compressed spring, to move axially, forcing the jaws into the conic chuck means and thereby produce a high radial gripping force between the jaws and the needle shaft. This force arises from the gradual narrowing taper of the cavity walls and the consequent high mechanical force advantage that this creates.

This arrangement is closely analogous to the familiar three-jawed drill chuck, where the axial force required to produce the required clamping force is usually developed by some form of screw thread. In this embodiment of the invention, the taper of the containment cavity is much more gradual, chosen consistently with the various parts to produce a self-locking action which increases as axial force is applied to the needle shaft in the same direction as the force of the pressure sleeve. It follows that motion of the needle shaft in the opposite direction will produce lessening of the grip of the locking jaws, but this may be resisted by selecting a spring for the pressure plate that is of sufficient strength to resist loosening of the clamping action.

In yet another embodiment of the invention, the locking jaws as described above may be replaced by rolling elements in the form of a plurality of substantially cylindrical rollers of hardened material, uniformly disposed about the axis of the needle shaft, with the axis of each roller in a plane perpendicular to the needle shaft axis, and with each roller making tangential, or crossed-cylinder contact with the surface of the needle shaft. The rollers are again contained in a gradually tapered cavity within the body of the guard device, each side of this cavity in this case being a plane surface forming part of a side surface of a conical polyhedron coaxial with the needle shaft.

In the unlocked state, these rollers are retained loosely in the bore by a surrounding containment cage, optionally constituted by an axial extension of the pressure sleeve as described above.

From its locked state, the pressure sleeve may be released to move axially, bringing the rollers into contact between the walls of the tapered cavity on the outside and the needle shaft on the inside. Subsequent axial motion of the needle shaft in this same direction of motion causes the rollers to roll axially with the needle towards the smaller end of the tapered cavity, increasing the force of contact between the tapered cavity wall and the needle shaft. This results in high frictional grip between the rollers and their containment cavity on the outside, and the needle shaft on the inside, sufficient to block further motion of the needle in this direction. Once jammed in this locking position continuing pressure from the pressure sleeve will tend to keep the protective guard in this locked condition.

In yet another embodiment of the invention, the rollers described above are replaced by a plurality of hardened spherical balls, uniformly disposed about the needle shaft axis, with the centers of the balls in a common plane perpendicular to the needle shaft axis, and with each ball making contact with the surface of the needle shaft. These balls may be contained within a gradually tapered conical bore or cavity within the body of the guard device, loosely confined within a containing cage which may be an axial extension of the pressure sleeve as described above.

In a further embodiment of the invention a sensing ball mechanism is employed in order to effect engagement of the protective guard to the needle. A locking assembly of the "chuck" type is provided within a main body that envelopes the needle by a transverse passage and is slidable thereon. This body is provided with a tapered or narrowing interior cavity which lies adjacent to the needle bore, and substantially may surround the needle shaft. A locking element conveniently, for the benefit purposes of symmetry, in the form of a pair of conically shaped locking jaws (although a single jaw element could be adopted) is present within the cavity, these locking jaws being displaceable between the broader and narrower regions within the interior cavity. A spring means is provided within the main body which biases the locking jaws towards the narrowing regions of the cavity whereby the locking jaws may be forced into jamming engagement between the needle bore and cavity wall, locking the protective guard to the needle.

A latch or latching means releaseably retains the locking element from advancement into the tapered cavity. A trigger means, based on a sensing element, operates to release the latching means when the tip of the needle is withdrawn into the protective guard, allowing the spring means to force the locking jaws into locking engagement with the needle.

In this embodiment this latching or retention means is of the ball-in-socket type wherein a latching ball lies partially within a groove or socket generally, or against a stopping surface, formed within the side of the locking jaws. This latching ball also partially rests against a stop surface formed on the interior of the main body of the guard. It is therefore inter-engaged with both elements. The pair of conical jaws are loosely inter-fitted with portions of each overlapping or interleaved with the other. This permits a single latching ball to be used to retain both of the jaws in their latched position.

The latching ball is held within the groove in the jaws by a further ball retention element, which may be in the form of a cylindrical sleeve or plunger which is able to slide from a position where it contains the latching ball within the groove on the jaws, to a position where it no longer contains the ball whereupon the ball may withdraw from the groove and release the locking jaws. This cylindrical sleeve retention element, therefore, serves as a release means for the jaws, thus forming part of the latching means.

A trigger means serves to hold the ball retention element in its ball-retaining position while the needle shaft passes entirely through the needle guard. Upon activation, this trigger means allows the retention element to be displaced to a ball-releasing position, once the needle tip is withdrawn within the protective guard.

This trigger means is of the sensing ball type wherein a steel ball serves as the sensing means for reacting to the presence or absence of the needle shaft within the guard. This sensing ball partially rests between a stop surface on the ball retention element and a further stop surface on the interior of the guard body. By reason of its contact with the stop surface on the ball retention element, this second ball prevents the ball retention element from moving and thereby releasing the first ball and latching system.

This sensing ball is, however, also retained in place by the needle shaft against which it rests, and towards which it is biased to move by pressure from the ball retention means. This pressure arises from a spring means which, conveniently may be the same spring means that applies pressure against the locking element. This second sensing ball is directed by the inclination of the further stop surface on the guard body to be displaced into the path of the needle. It is blocked from so moving by the needle, so long as the needle passes fully through the guard.

Once the tip of the needle is withdrawn into the guard past the sensing ball, leaving this second or sensing ball no longer in contact with the needle the sensing ball will move into the path previously occupied by the needle. This displacement of the sensing ball then allows the ball retention element to move sufficiently to release the latching ball, and thereby release the jaws in order to effect locking of the guard to the needle.

Thus, in this embodiment the latching means is distinctly removed from the trigger means, and two independent parts, the latching ball and the sensing ball must both be displaced from their positions in order for locking to occur.

The locking force of the jaws within the chuck is enhanced by any attempt to further remove the guard from the needle. Conversely, it is reduced by an attempt to cause the needle tip to re-emerge from the guard. Conveniently, the presence of the sensing ball in the needle path can serve to prevent such a re-emergence.

Thus, we summarize these embodiments as providing a tip protective guard for covering the tip of a needle of comprising:

(1) a main guard body provided with a passage therethrough capable of enveloping a needle inserted therein, said body contains a narrowing interior cavity that provides an angled jamming surface;

(2) a locking element or jamming means slidable within said cavity capable of locking relative movement between said needle and said body in at least one axial direction of said needle;

(3) spring means capable of biasing said jamming means to advance into the narrowing interior of said tapered cavity and lockingly engage said needle in at least one axial direction of said needle;

(4) latching means positioned to releaseably restrain said jamming means from being advanced into said cavity;

(5) trigger means, positioned to release said latching means when the tip of said needle is withdrawn into said guard body; and (6) containment means for preventing re-emergence of said needle tip from said body once the needle tip has been withdrawn into said body.

In yet another embodiment of the invention, the angled surface described above is carried by a canting funnel held in place in its orientation by a lever arm.

This funnel and lever arm may be formed of a flat, hardened strip, bent in the shape of a broad U to provide a tapered funnel lying in the plane of the needle shaft, nearly coaxially with the needle and with the lever arm extending from the funnel in the direction of the funnel's opening.

The lever arm, which serves as an alignment means for the canting funnel, is contained within the body of the guard device. An end of the funnel remote from the lever arm is held in contact with the body of the guard device by the force of a helical compression spring. The funnel's point of contact with the internal face of the body serves as a pivot point and clearance is provided for the funnel and lever arm to pivot about this pivot point. The spring is seated within a cylindrical cavity in the body on the opposite side of the needle shaft from the pivot point, the axis of the funnel being close to and, initially, nearly or substantially parallel with the needle axis. The free end of the spring extends from its seat to press against the outer, central end of the funnel on the side remote from the lever arm and pivot point. This biases both the funnel and the leg of the lever arm to rotate with respect to the needle shaft, the lever arm being urged towards the needle. With the needle extending through the body of the guard device, the lever arm is constrained by the contact of its outer end with the side of the needle shaft. So long as this contact occurs, the lever arm maintains the orientation of the funnel unit with respect to the needle axis.

When the guard is slid along the needle so that the tip end of the needle has entered the guard body and moved past the point of contact with the end of the lever arm, the lever arm is freed to turn about the pivot point under spring pressure applied to the funnel. This causes the funnel to cant with respect to the needle. The spring then forces a jamming element, preferably in the form of a hardened ball, into the newly-formed, tapered gap existing between the inner surface of the funnel and the needle. This action causes substantial frictional contact and locking engagement between the guard body through the hardened ball and the needle shaft.

With the selection of the known appropriate geometry of the funnel's inner jamming surface and needle shaft, critically related to the coefficient of friction between them, the frictional grip between the jamming element and the needle shaft may be arranged to always be greater than the applied axial force on the needle. Thus further axial motion of the needle in at least one direction is prevented until material failure occurs.

By way of further security, the needle-contacting end of the lever arm is provided with a blocking plate which becomes displaced into the needle path once the needle is no longer in contact with the plate-carrying end of this leg. This serves to block the reverse displacement of the needle, ensuring the complete containment of the needle tip within the protective guard.

A loosely-fitting cylindrical sleeve surrounding the body of the guard is preferably added in all cases to provide rotational isolation from the means used to move the guard axially on the needle shaft, thereby preventing the forcible removal of the protective guard by accidental or deliberate twisting of the guard relative to the needle. Such a sleeve may optionally be applied to all embodiments of the protective guard.

A catheter with an insertion needle or wire is particularly suited to carry a needle tip protector of the type described.

The foregoing constitutes a description of a series of exemplary modes by which the protective guard may be clamped or locked in place so as to conceal a needle tip. These mechanisms all rely upon introducing a jamming element into a tapering space existing between a needle and a jamming surface. Details of these mechanisms are further described in the following sections in conjunction with the description of the preferred embodiments.

The foregoing summarizes the principal features of the invention and some of its optional aspects. The invention may be further understood by the description of the preferred embodiments, in conjunction with the drawings, which now follow.

BRIEF SUMMARY OF THE DRAWINGS

FIG. 8 is a partial cross-section of the device in an embodiment incorporating jaws within a chuck, shown in its unlocked state;

FIG. 9 is a cross-section of FIG. 8 showing an end view of the locking jaws, viewed from within;

FIG. 12 is a partial cross section of the device in the embodiment incorporating locking rollers within a tapered cavity, shown in its locked state;

FIG. 13 is a cross sectional end view of FIG. 12;

FIG. 14 is a partial perspective view of the locking sleeve portion of FIG. 12, showing the placement of the locking rollers within their containment means;

FIG. 15 is a partial cross-section of the device in the embodiment incorporating locking balls within a conical bore, shown in its locked state;

FIG. 16 is a cross-sectional end view of FIG. 15;

FIG. 17 is a partial perspective view of the locking sleeve portion of FIG. 15, showing the placement of the locking balls within their containment means;

FIG. 18 is a partial cross-section of the device in the alternate embodiment employing locking leaves and a needle sensing and trigger mechanism, shown in its unlocked state.

FIG. 19 is a partial cross-section of FIG. 18 showing the latch shaft in its unlocked position.

FIG. 28 shows a catheter hub with needle protector in cross-section, based on a double trigger mechanism utilizing on a ball-latch and sensing ball system, in cocked condition;

FIG. 29 shows the device of FIG. 28 in transition to grasping the needle;

FIG. 30 shows the device of FIG. 28/with the needle grasped by the guard element and deployed as a protector over the needle tip;

FIG. 31 is a side view of the jaw element of FIG. 28;

FIG. 32 is an end view of the jaw element of FIG. 28;

FIG. 33 is a further side view of the jaw element of FIG. 28;

FIG. 39 is a longitudinal section of the device of FIG. 37 in its locked state, after use of the needle and deployment of the needle guard.

FIG. 40 is a cross-sectional view of the locking mechanism of FIG. 37 in the locked state, fitted to a large-diameter needle.

FIG. 41 is a cross-sectional view of the locking mechanism of FIG. 37 in the locked state, fitted to a small-diameter needle.

FIG. 43 is a side view of the locking arm of FIG. 37.

FIG. 44 is a top view of FIG. 43.

FIG. 45 is a bottom view of FIG. 43.

FIG. 46 is a right-end view of FIG. 43.

FIG. 47 is a left-end view of FIG. 43.

FIG. 48 is a cross-sectional view of the funnel portion of FIG. 43.

FIG. 49 is a side view of the inner body of the device of FIG. 37.

FIG. 50 is a left-end view of FIG. 49, showing the needle being inserted during assembly.

FIG. 51 is a top view of FIG. 49.

DETAILED DESCRIPTION OF EMBODIMENTS

Figure 1:
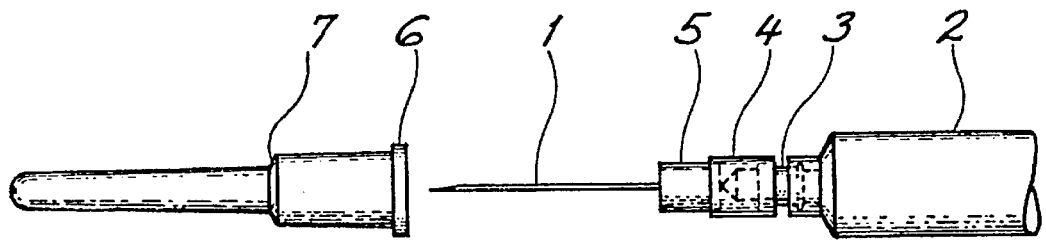
FIG. 1 shows a hypodermic needle fitted with the subject guard device, mounted on a syringe, and with the needle removed from its protective sheath preparatory to use.

Referring to FIG. 1, the hypodermic needle 1 is attached to the syringe 2 by a needle connector or base element 3 of conventional design as regards its attachment to the syringe. The needle is optionally provided with a guard retainer 4 in the form of a hollow cylinder coaxial with the needle, with one end attached to the needle connector element 3, and with its other end directed towards the opposite or tip-end of the needle. This cylinder 4 attaches frictionally to the outer circumference of the guard device 5, hereinafter referred to as the "guard" or "protective guard".

The guard may be removed axially from the guard housing 4 with normal finger effort, and thereafter may be slid axially with slight or no frictional resistance along the length of the needle. Alternately, the retainer 4 may be detached from the base 3 and used as a gripping means to slide the guard along the needle. While the retainer 4 provides convenience in coupling and handling the parts of the needle assembly, it is purely optional. If omitted, the guard 5 may be provided with a tight sliding fit on the needle 1 that will allow it to be stored on the needle 1 near the base 3 without use of the retainer 4.

Prior to use, the needle 1, guard retainer 4, and guard 5 may be stored in a protective sheath 6 of conventional design. The sheath 6 may be frictionally retained axially on the retainer 4 by inwardly-directed detent projections on the inner bore of the sheath entry opening, following well-established practice. Such established practice allows the needle to be retained within and gripped by the protective sheath while fitting the needle to the syringe or other device. The frictional coupling between the sheath 6 and retainer 4 is selected to release more easily than the coupling between the retainer 4 and needle base 3. This allows for removal of the sheath 6 without disturbing the retainer 4 or guard 5. The sheath 6 may optionally be provided with an inner shoulder 7 which will axially bias the guard 5 towards its stored position inside the retainer 4.

Figure 2:
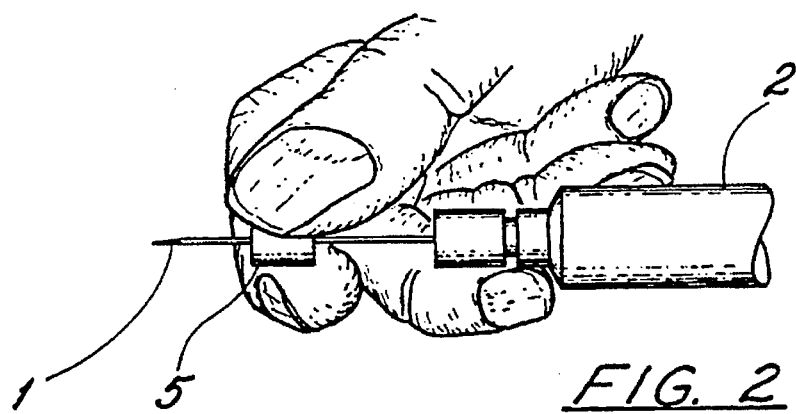
FIG. 2 shows the needle following use, with the subject guard device being slid towards the end of the needle by hand as the first step in the disposal sequence.

Referring to FIG. 2, all motions of the guard 5 during the disposal process are axial and directed away from the point of the needle 1, with the hands held away safely to the rear of the latter. Provided the guard 5 is not slid beyond the point of the needle 1, it may be slid in either direction along the needle, and may be returned to its stored position in the retainer 4 if desired. While frictionally stored in and when released from its retainer 4 the guard 5 is in its unlocked state.

Figure 3:
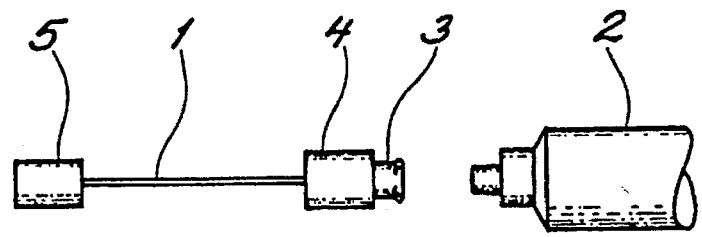
FIG. 3 shows the guard device locked automatically over the end of the needle, and the needle removed from the syringe for disposal.

As shown in FIG. 3, when the guard 5 reaches the end of the needle 1, and when the point of the needle is entirely enclosed within the guard, an armed locking mechanism within guard 5 is released to firmly grip the guard to the needle 1. Preferably, as shown in the exemplary trigger mechanisms described next, the opening in the outer end of the guard is closed-off to completely cover the point of the needle against accidental protrusion, even in the event of failure of the locking mechanism to hold the guard in place against impact, such as may be caused by dropping the needle and attached syringe. The guard 5 is now in what is referred to herein as its locked state.

Figure 4:
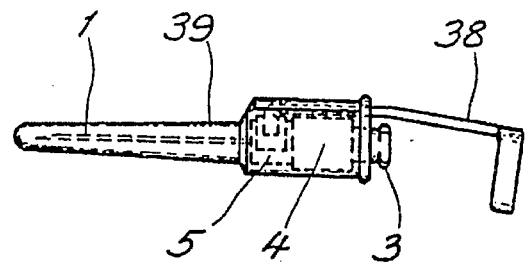
FIG. 4 shows an embodiment of the guard device in its protective sheath prior to use, this embodiment including a detachable handle on the guard device.

In instances where it is desirable to increase the separation between the operator's fingers and a possibly contaminated needle, a further embodiment provides a detachable handle to allow the operator to slide the guard device along the needle from a safe distance. FIG. 4 shows this embodiment, where detachable handle 38 is frictionally attached to guard 5, and the assembly of needle 1, guard 5, and handle 38 are encased in protective sheath 39, ready for use. The entry of protective sheath 39 is provided with a with a key-hole shaped cross-section to accommodate handle 38, and the other retaining features described above would also be included in the entry of this sheath.

Figure 5:
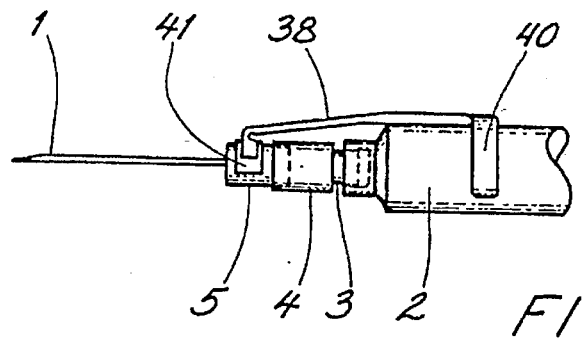
FIG. 5 shows the device of FIG. 4 removed from its protective sheath and mounted on a syringe, ready for use.

In FIG. 5, syringe 2 has been fitted to the needle connector or base 3, the circular clip 40 of handle 38 has been snapped over the body of syringe 2 for retention, and the needle and guard assembly has been removed from the protective sheath ready for use. Handle 38 is frictionally attached to guard 5 by circular clip 41.

Figure 6:
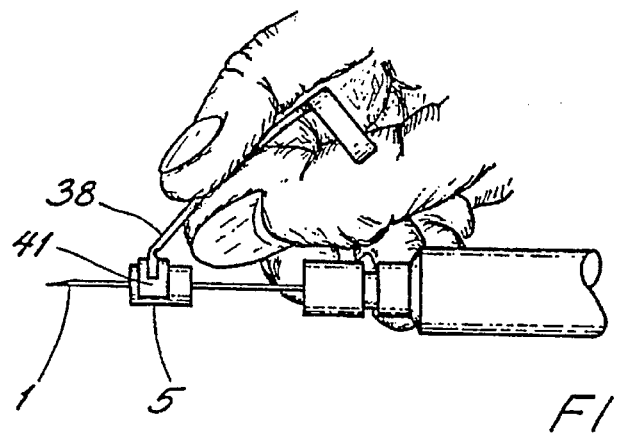
FIG. 6 shows the device of FIG. 5 following use of the needle, with the protective device being moved along the needle with the detachable handle.
Figure 7:
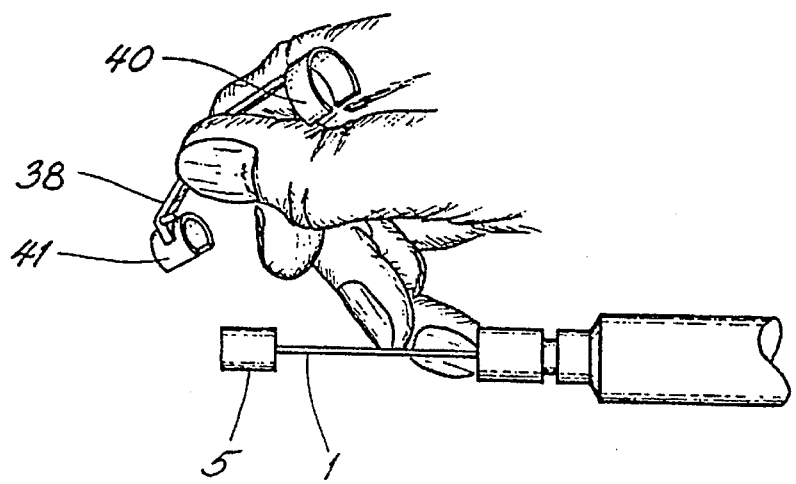
FIG. 7 shows the device of FIG. 5 with the protective device locked on the end of the needle and the detachable handle pulled free for disposal.

FIG. 6 shows guard device 5 being slid along needle shaft 1 following use, using handle 38. When guard 5 locks on the end of needle 1, handle 38 may be detached for disposal by pulling or twisting, as shown in FIG. 7.

Figure 10:
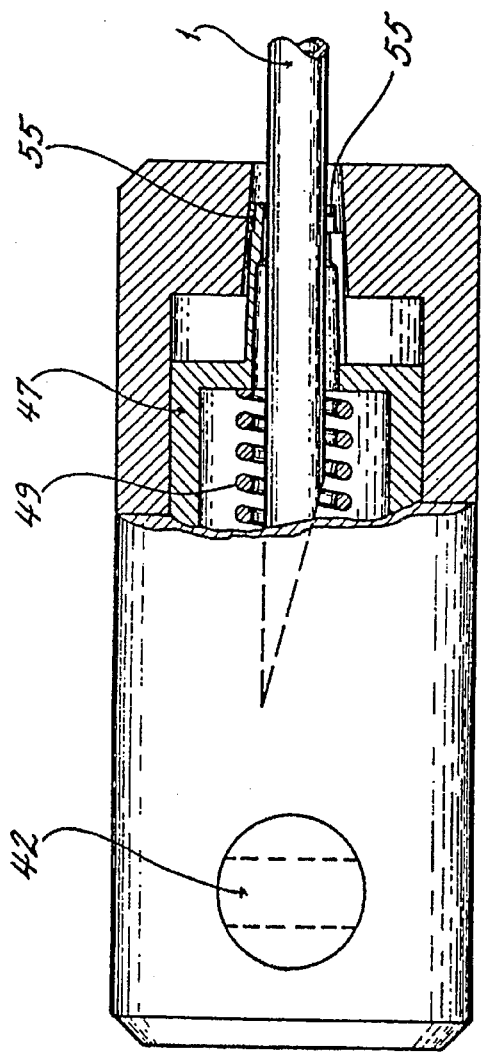
FIG. 10 is a partial cross-section showing the device of FIG. 8 in its locked state.
Figure 11:
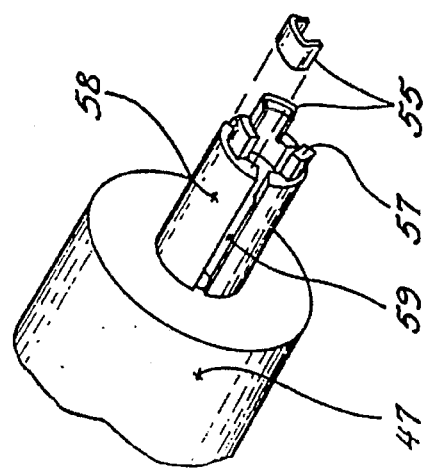
FIG. 11 is a perspective view of the device of FIG. 8 showing the locking jaws and their means of retention.

FIGS. 8 and 10 show a first example of locking system before and after engagement. The general locking means comprises three locking jaws 55 contained in a gently tapered conical cavity in the form of a bore 56 in the chuck body 43. In this example, these jaws are formed from sheet material into an approximately C-shaped cross-section and then hardened although alternate forms may be used. These are arranged uniformly about the needle shaft as shown in FIG. 9, and are retained loosely in this position by fingers 57 extending axially from the end of pressure sleeve 47, and fitting inside the jaws 55. This is shown in FIG. 11, one jaw being omitted for clarity.

Fingers 57 extend from a reduced portion or spigot 58 of pressure sleeve 47, to allow entry of the latter into bore 56 during locking. This spigot is provided with axial slots 59 as shown in FIG. 11 to allow its outer end to collapse slightly in diameter as it is forced into the tapered bore 56. Further elasticity is imparted to this spigot bore 60, shown in FIG. 8, by a reduction in its wall thickness in the vicinity of its junction with the main body of the pressure sleeve 47. A greater wall thickness is retained at its outer end where it presses against the locking jaws 55.

In the locked state, pressure sleeve 47 is released by latch 42 described further below and its spigot drives jaws 55 into the narrowing annular space 56 between the needle shaft 1 and the tapered bore 56, forcing the jaws 55 against the needle shaft 1. Contact between the two is made along the narrow rectangular edges of the C-shaped jaws 55. By finely serrating these edges in the blanking stage of forming the jaws, the coefficient of friction between jaw and needle shaft may be substantially increased.

By providing a suitable length of tapered bore 56, this clamping means can accommodate a range of needle diameters.

A further embodiment is shown in FIG. 12, wherein the general locking means comprises a plurality of locking rollers 61 of hardened material, two being shown in this example. These are loosely contained in an axially tapering cavity 62 of substantially rectangular cross-section in the body 43 of the guard device. Each locking roller 61 is loosely retained within a substantially rectangular cavity 63 in a rectangular extension 64 of pressure sleeve 47, with the axis of each locking roller 61 in a common plane perpendicular to the axis of the needle shaft 1, and with each roller 61 uniformly disposed about the axis of needle shaft 1, as shown in FIG. 13.

In the unlocked state, the pressure sleeve 47 is held by the latch 42 against the pressure of the spring 49 as described above, such that the locking rollers 61 are held loosely by extension 64 in the larger portion of the tapered cavity 62, making no significant contact with the walls 65 of the cavity 62 or with the needle shaft 1. In this state, the needle shaft 1 is free to move both axially and rotationally within its bore 92 in the guard device.

In the locked state, as shown in FIG. 12, the latch 42 releases the pressure sleeve 47 by the same action as described further below to move under pressure of spring 49 towards the narrowing end of cavity 62 as described above, so that extension 64 carries the locking rollers 61 into contact with the wall 65 of the tapering cavity 62 on the outside and the needle shaft 1 on the inside. Motion of the needle shaft i relative to the body 43 in the same direction as the spring directed motion of pressure sleeve 47 will cause the locking rollers 61 to roll further into the gradually narrowing end of cavity 62, exerting a high radial pressure against the wall 65 and the surface of the needle shaft 1. This prevents further motion of the needle by frictional grip between the rollers 61, the cavity walls 65, and the needle shaft 1.

By providing a suitable length of tapered cavity 62, this clamping means can accommodate a range of needle diameters from any arbitrary maximum value down to near zero.

A further alternate embodiment is shown in FIG. 15, wherein the general locking means comprises a plurality of locking balls 66 of hardened material, three being shown in this example, as more clearly seen in FIG. 16. The balls 66 are loosely contained in an axially tapering bore 67 of circular cross-section in the body 43 of the guard device. Each locking ball 66 is loosely retained within a cage optionally composed of a substantially cylindrical cavity 68, the axis of each said cavity being perpendicular to the needle axis in a cylindrical extension 69 of pressure sleeve 47. The center of each locking ball 66 lies in a common plane perpendicular to the axis of the needle shaft 1, and the balls 66 are disposed uniformly about the needle shaft 1, as shown in FIG. 16. In all other respects, the action of the locking halls 66 in the locked state is similar to that of the locking rollers 61 as described above.

By providing a suitable length of tapered bore 67, this clamping means can accommodate a range of needle diameters from any arbitrary maximum value down to a minimum diameter determined by the point at which the locking balls come into contact with one another. When three balls are used, this minimum needle diameter is theoretically approximately 0.155 of the diameter of the locking balls. Considerations relating to the retention of the locking balls place a practical limit of approximately 0.3 of the ball diameter. The minimum diameter of needle which can be gripped becomes progressively larger as more than three balls of a given size are used.

Thus, three alternate embodiments have been described which rely on a narrowing cavity to achieve the locking effect. The latch and trigger mechanism referenced for each case has been of a type that relies on a transverse rotating cylinder. Alternate latch and trigger system could be substituted, relying, for example, on the later described sensing ball or lever arm types of systems.

For completeness of understanding, the transverse rotating cylinder latch will now be described with respect to an alternate "push-nut" needle engagement system.

Figure 24:
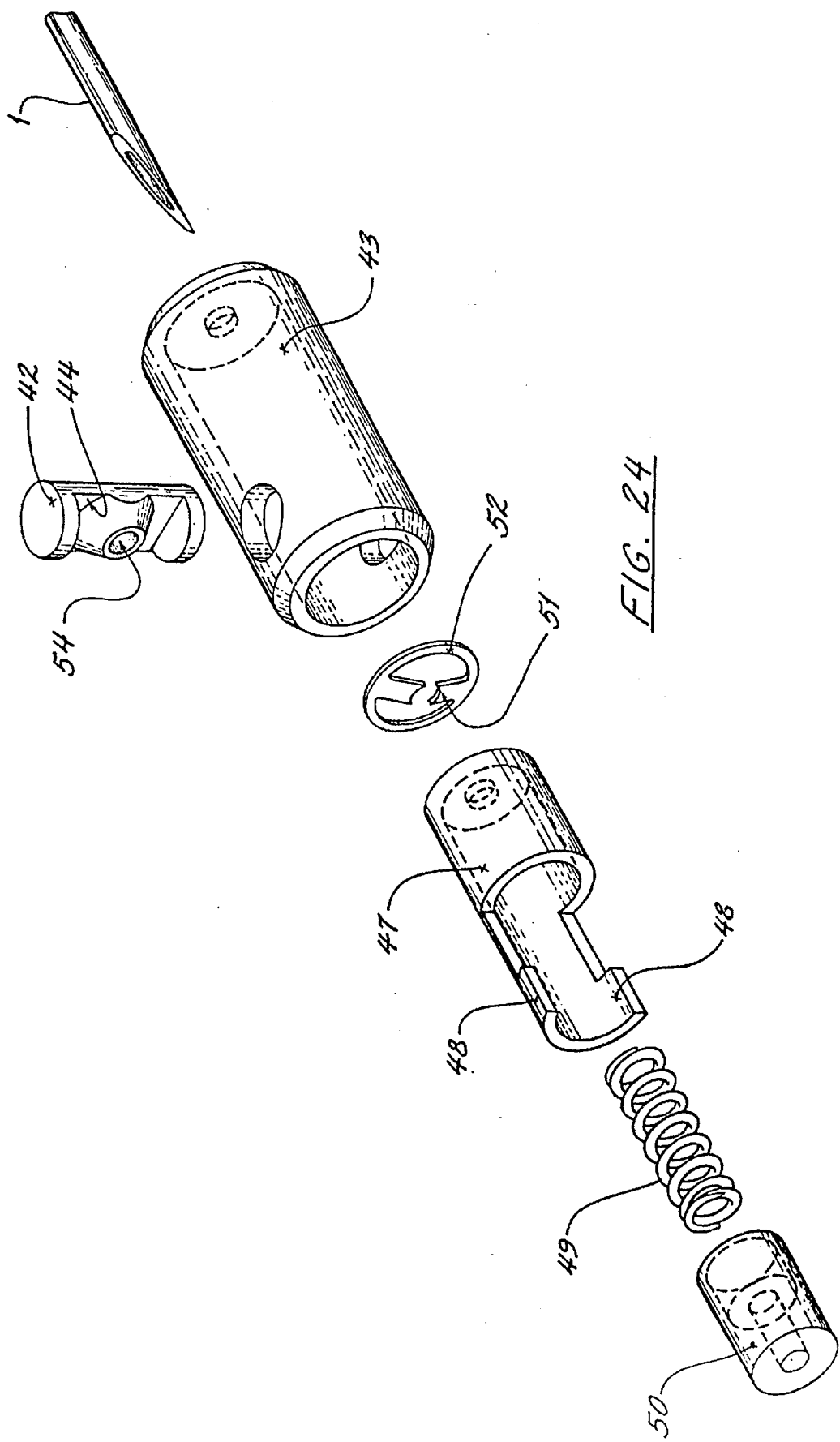
FIG. 24 is an exploded perspective view of the device of FIG. 22.

The generally assembly of the components for this embodiment may be seen in exploded view FIG. 24 wherein a pair of locking leaf elements 51 are mounted on a rim 52 within a body 43, coaxially with the needle 1.

Referring to FIG. 18, latch shaft 42 is mounted transversely in the body 43, a portion of the left side of latch 42 is relieved to form a flat surface 44 in the axial plane on either side of an unrelieved center portion 45, through which the needle shaft passes at right angles to the latch axis, thus preventing its rotation in the body 43.

Sliding axially in the bore 46 of body 43 is pressure sleeve 47, in the form of a hollow cylinder, largely closed at the right end. A portion of its left half is cut away to form bifurcated arms 48 which engage the plane surfaces 44 of latch 42, thus preventing motion of the pressure sleeve to the right when latch 42 is in the position shown.

Figures 20, 21:
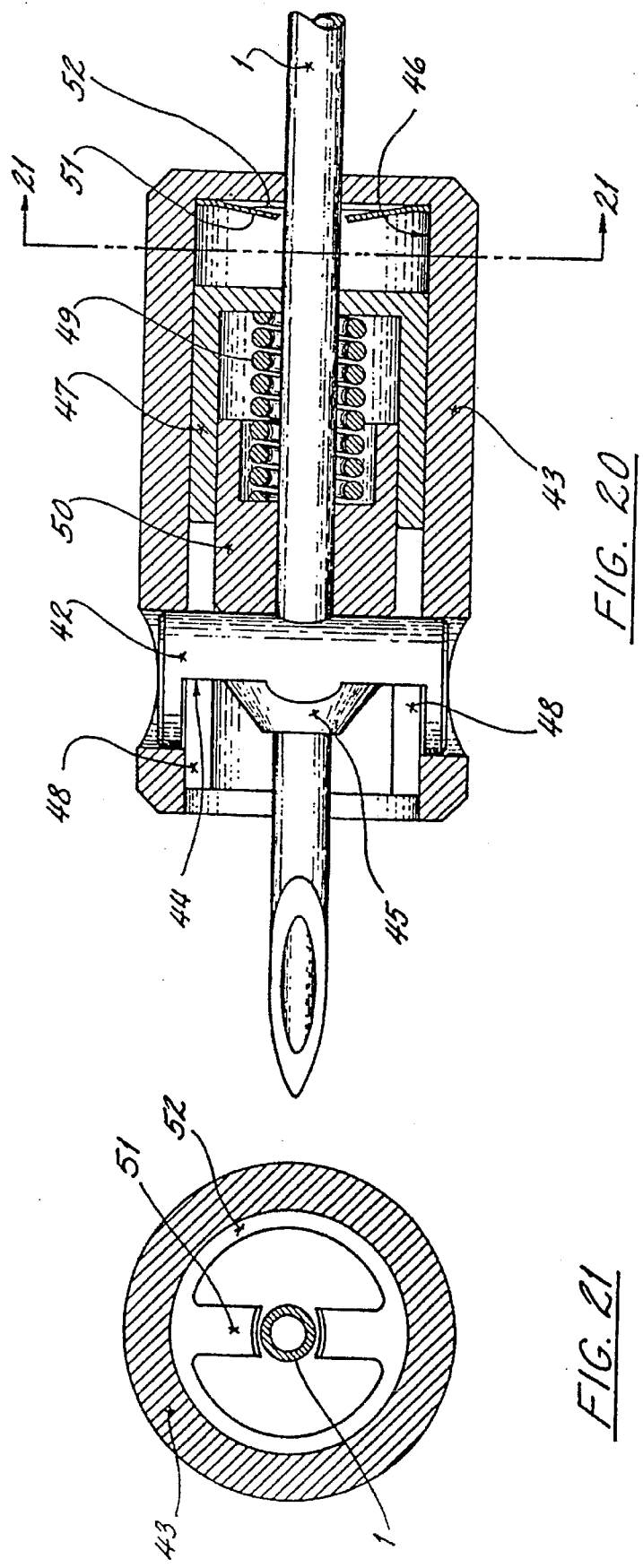
FIG. 20 is a cross-section of the device of FIG. 18 in its unlocked state, rotated ninety degrees from FIG. 18.
FIG. 21 is a cross-section of FIG. 20 showing the locking leaves in their unlocked position, viewed from within.

Referring to FIG. 20, pressure sleeve 47 is pressed to the right by compression spring 49, whose leftwards reaction is taken by spring plunger 50, sliding freely within sleeve 47, and which presses against latch 42. The latter 42 holds plunger 47 away from the ends of locking leaves 51, which are retained in bore 46 by retaining rim 52, integral with leaves 51. The rim 52 is deflected out of its free form to produce a slight interference fit in bore 46, thereby allowing it to be retained at the bottom of the bore.

The locking leaf assembly is shown in FIG. 21, two leaves being shown in this example. Optionally one leaf or more than two leaves could be employed with equivalent results. In FIG. 20 spring pressure to the right on sleeve 47 is transmitted to the plane surfaces 44 of latch 42 by arms 48, the ends of which are radially separated from the axis of latch 42 by distance 53. This forms a small turning moment tending to cause rotation of the latch in a clockwise direction as viewed in FIG. 18, this rotation being prevented by the needle shaft passing through the axis of the latch.

Figure 22:
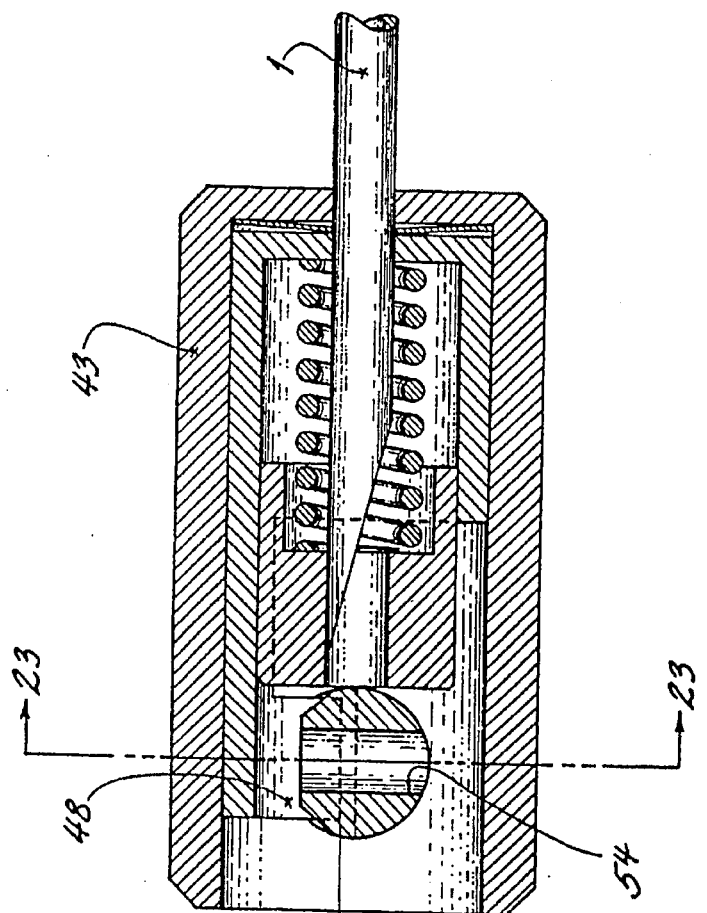
FIG. 22 is a cross-section of the device of FIG. 18 in its locked state.
Figure 23:
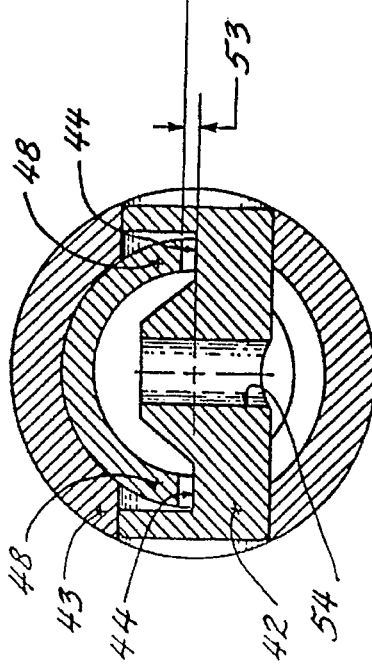
FIG. 23 is a cross-section of FIG. 22 showing the latch in its locked position.

In FIG. 22, needle 1 has been withdrawn until its tip is inside body 43 and free of latch 42, allowing the latter to rotate until its plane surfaces 44 are parallel with the axis of pressure sleeve 47. This allows the latter to slide to the right past the latch and apply spring pressure to the ends of locking leaves 51, pressing them against the needle shaft 1. This locks the latter in position, preventing further motion to the right, relative to the body. The continued engagement of the arms 48 of sleeve 47 with the cut-away portions of latch 42 prevents the latter from falling out of body 43, and from rotating significantly about its own axis.

The needle is now prevented from withdrawing from body 43 to the right, and as latch 42 is now turned and locked in position with its needle held 54 at right angles to the needle axis, the needle point cannot re-emerge from the left end of the body, even though the one-way locking action of leaves 51 may permit motion in this direction.

The foregoing description has, therefore, shown one form of needle sensing latch and trigger mechanism.

A further such alternate mechanism will be described below in conjunction with an additional needle-engagement system mounted on a catheter/needle assembly. The use of the guard on such an assembly will first be described.

Figure 25:
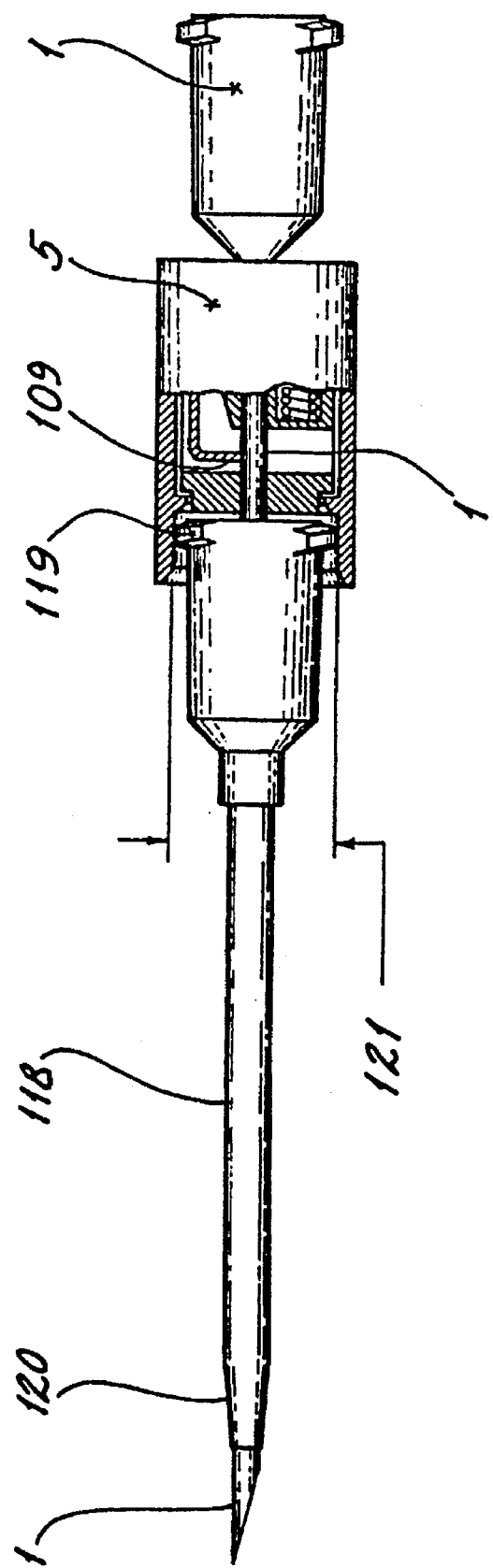
FIG. 25 shows the guard device of FIG. 37 fitted to an intravenous catheter assembly, prior to insertion into a patient.
Figure 26:
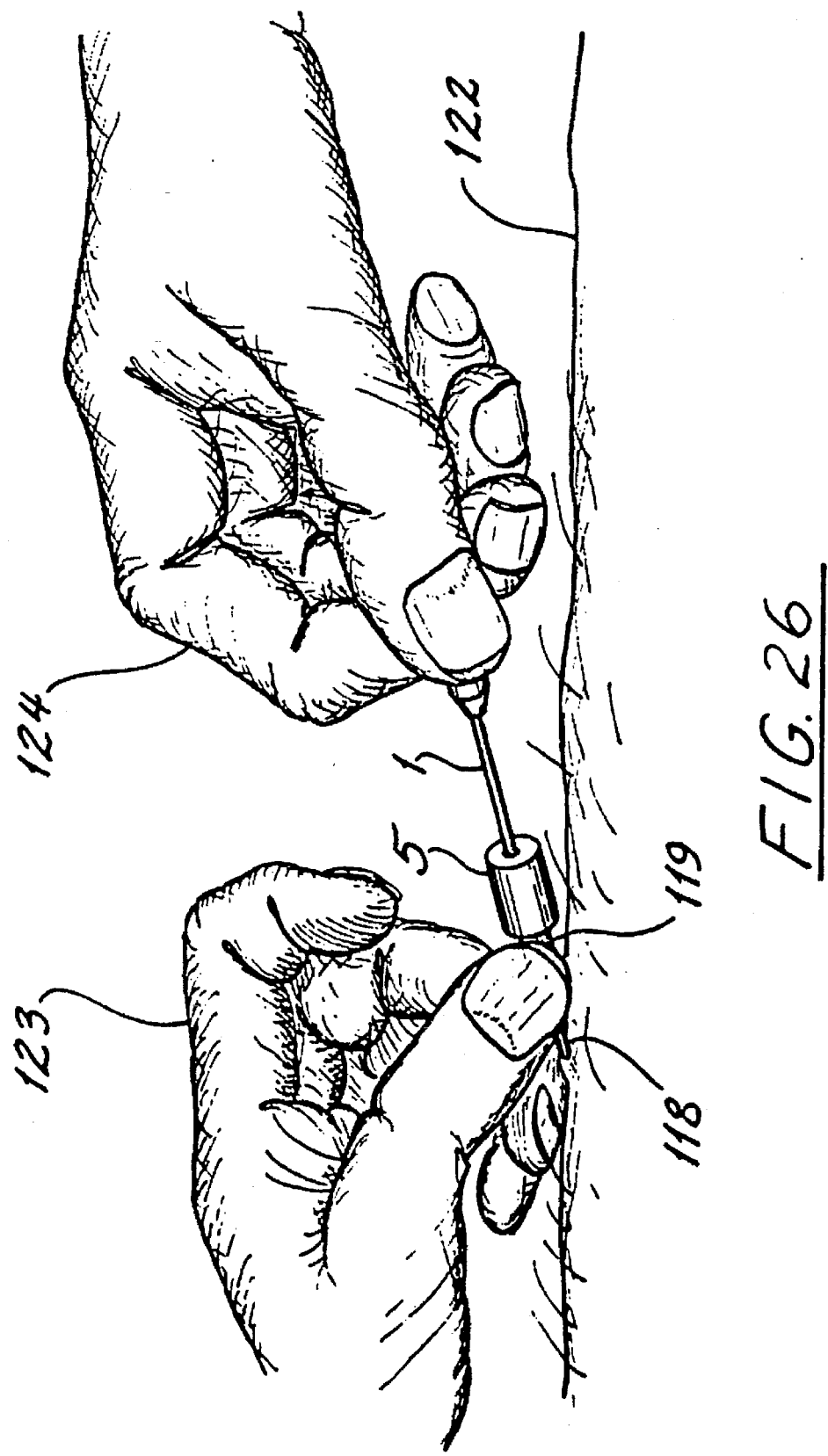
FIG. 26 shows the catheter inserted into a patient with the guard in place on the catheter and the needle being withdrawn.
Figure 27:
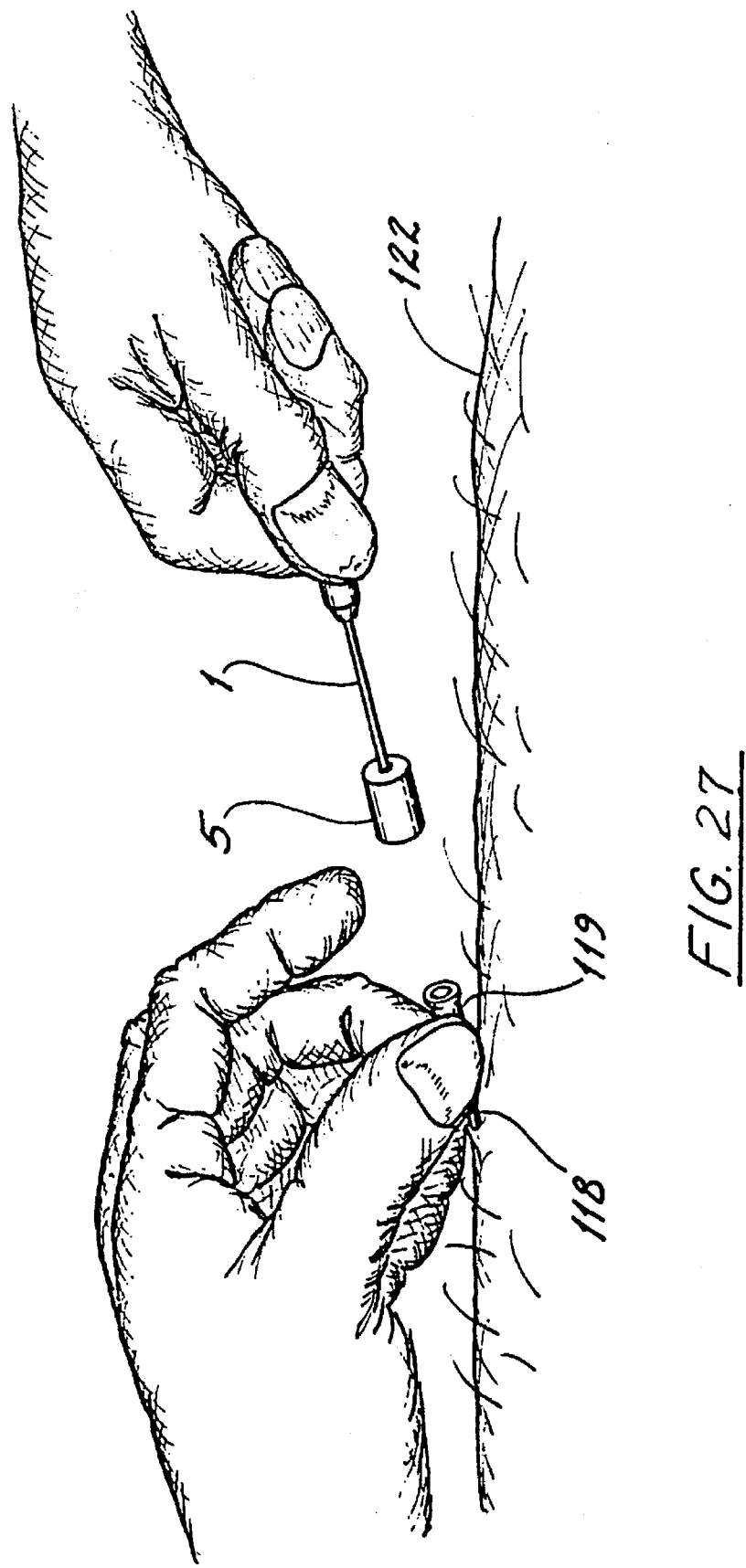
FIG. 27 shows the needle fully withdrawn from the catheter with the guard locked over the point of the needle.
Figure 34:
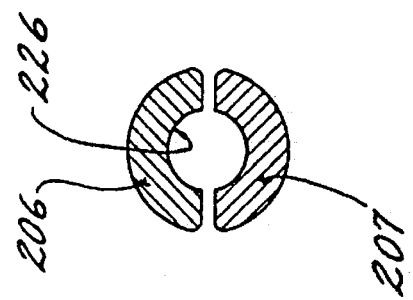
FIG. 34 is an end view cross-section through FIG. 33.
Figure 35:
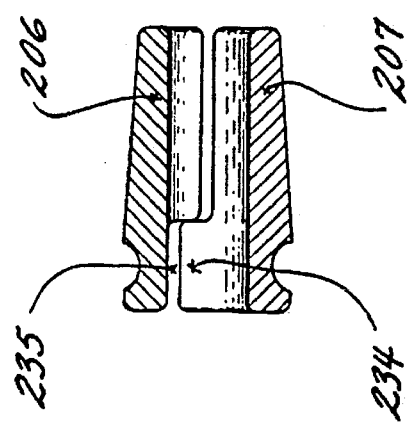
FIG. 35 is a side view cross-section through FIG. 32.

FIG. 25 shows the protective guard device 5 fitted to a needle 1 and attached to a catheter 118 as part of an intravenous catheter assembly. The outer shell 113 of the guard extends over and is frictionally retained on the tubing attachment chuck 119 or base of the catheter 118. The needle 1 extends through the guard 5 and the catheter 118 to emerge slightly beyond the distal end 120 of the catheter. The needle may be moved freely within the catheter 118 in any direction, either axially or rotationally, impeded only by the slight drag of the latch 109 of guard 5 and the constriction of the reduced end 120 of the catheter tube 118.

The inner diameter 121 of the extended portion of shell 113 is such as to provide a frictional axial retention force between shell 113 and catheter chuck 119 significantly greater than the maximum axial drag of needle 1 within guard 5, and comparable to the initial axial retention familiarly encountered between the needle and catheter in a conventional intravenous catheter assembly. This retains guard 5 on catheter chuck 119 during needle withdrawal, as shown in FIG. 41. Here the operator has inserted needle 1 and catheter 118 into a blood vessel in the patient 122, and is withdrawing needle 1 from catheter 118 through guard 5, holding catheter 118 in place with one hand 123 and holding needle 1 with the other hand 124. The guard 5 remains frictionally retained on chuck 119 of the catheter.

Figure 42:
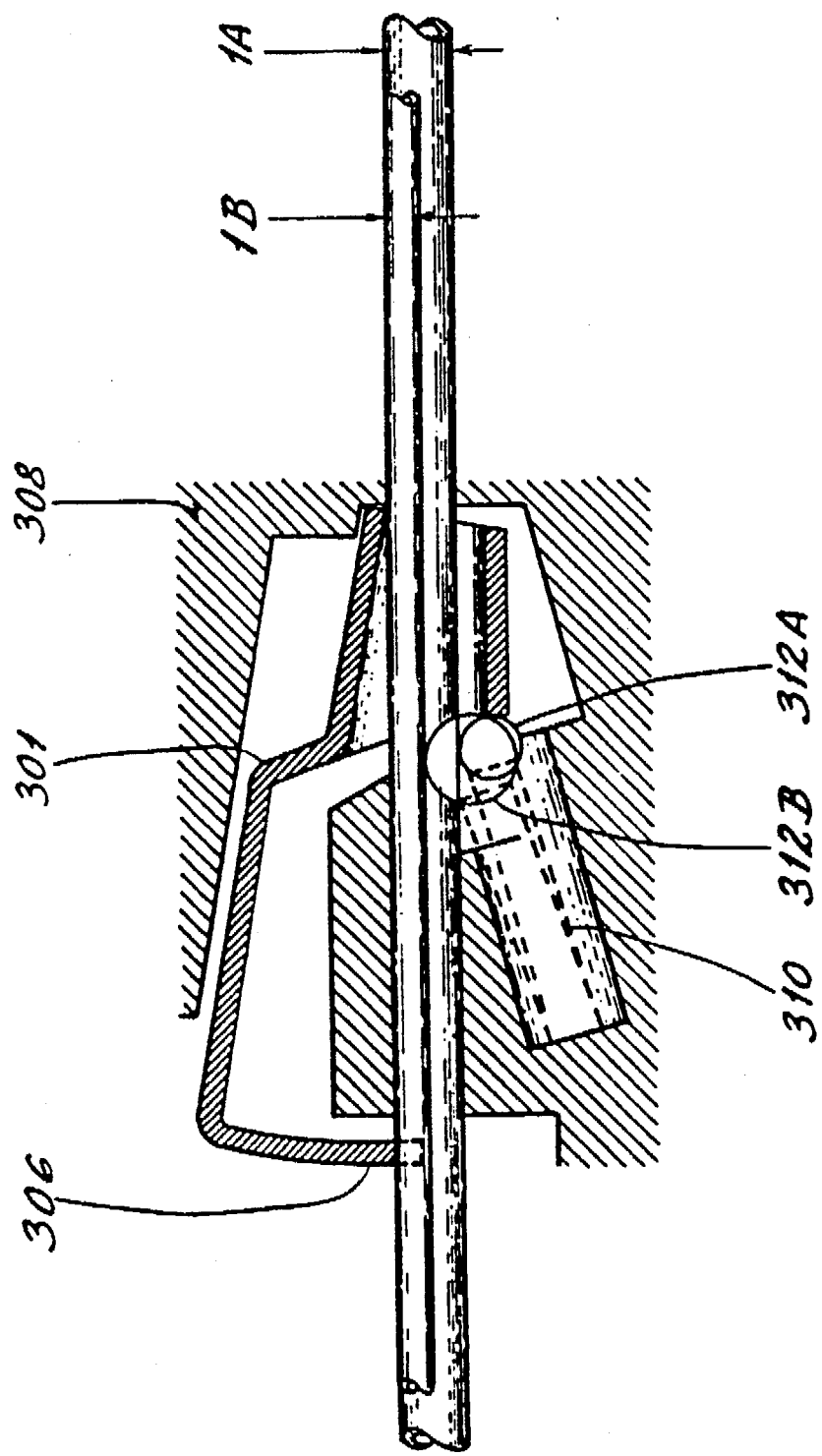
FIG. 42 is a partial longitudinal section of the unlocked device of FIG. 37, with two needle sizes and two locking balls superimposed.

When the needle point passes into the body of the guard 5, the guard 5 locks automatically onto needle shaft 1, the operator exerts a slightly increased withdrawal force on the needle, sufficient to release guard 5 from catheter chuck 119, as shown in FIG. 42. The operator can now dispose of the protected needle without further action, while attending to the catheter tube attachment.

A further embodiment is shown in FIGS. 28 to 36. This version relies on a ball-latching mechanism to maintain the guard in a cocked condition, and a sensing-ball arrangement to serve as the trigger. This embodiment is shown in a form adapted to be installed on a catheter assembly. It could equally be applied to a straight needle, as used on a syringe.

Prior to use, the needle guard assembly FIG. 28–36, inclusive, is housed largely within the base of the catheter 209. The guard base 201 provides radial support for the base 210 of the needle 1 but does not fictionally retain it axially. The guard shell 202, which is retained on guard base 201 by snap-fit shoulders 212, has an outer surface tapered to fit the correspondingly tapered bore 213 of the catheter base 209, with moderate axial frictional retention therein.

During insertion of the catheter, the necessary axial thrust is transferred from the face 214 of the needle base 210 to the guard base 201 and thence through face 215 of the latter to catheter base 209, without affecting the respective radial fits described the paragraph directly above.

During withdrawal of the needle from the catheter, the needle base 210 readily releases from the guard base 201, while the latter is axially retained within the catheter base 209 by the greater frictional grip between the two.

With the needle 211 passing wholly through the needle guard assembly as in FIG. 28, interval plunger 203 is urged towards the pointed end of the needle 211 by compression spring 204, but is prevented from moving axially by the three-point confinement of sensing ball 205, which makes contact with plunger 204 against the latter's perpendicular end face at point 216, against the sloping internal end face 227 of guard shell 202 at point 217, and against the needle shaft 211 at point 218. The sensing ball 205 is free to move orbitally about the needle axis in the annular space 219 surrounding the needle.

The reactionary force at the opposite end of spring 204 acts against the perpendicular end face of the pair of locking jaws 206 and 207, but motion of these latter parts is prevented by the confinement of latching ball 208. This makes contact with jaw 207 on the curved side of its guard 220 at point 221, with the perpendicular end face of guard base 201 at point 222, and with the cylindrical inner surface of plunger 203 at point 223. Axial motion of locking jaw 206 is prevented by its being axially locked to jaw 207 as will be described below. Latching ball 208 is free to move orbitally about the needle axis in the annular space 224 surrounding locking jaws 206 and 207.

With jaws 206 and 207 held axially as shown in FIG. 29, their tapered outer surfaces are confined within the correspondingly tapered inner bore 225 of guard base 201 to an extent sufficient to radially support the needle shaft 211 on the cylindrical inner surfaces 226 of the locking jaws, yet without developing sufficient frictional contact to significantly impede the axial movement of the needle shaft through the jaws.

Similarly, the pressure of plunger 203 against sensing ball 205 is re- directed by contact point 217 to produce a reduced force at contact point 218, such that the frictional force between the polished surfaces of sensing ball 205 and needle shaft 211 negligibly impedes the axial movement of the needle shaft 211 within the needle guard.

As the point of the needle enters the needle guard during withdrawal, sensing ball 205 passes over the end of the needle, following the inclined inner end face 227 of body shell 202, under the axially-directed urging of plunger 203, driven by spring 204. The greatest extent of this motion before the sensing ball 205 becomes free of the needle occurs with the bevel 228 of needle 211 rotationally oriented to be tangent with the surface of ball 205 as shown in FIG. 29, and with the point of tangency 229 being on the end of a line passing through the centre of the sensing ball 205 to an opposite point of contact 230 between the sensing ball 205 and the corner of ball socket 231 in the end of guard shell 202.

It will be seen that the configuration in FIG. 29 is a critical one, in that reversal of the needle withdrawal motion will not cause the ball to likewise reverse its motion towards the configuration of FIG. 28, because the force exerted on the ball by the tangential face 228 of the needle acts on a line through the centre of the ball, and therefore cannot move it in any direction. It will be seen further that when the configuration of FIG. 29 is reached, the spring-driven plunger 203 will force sensing ball 205 free of the needle 211, and drive it into ball cavity 231, as shown in FIG. 30.

With the configuration of FIG. 29, the geometry of the containment of latching ball 208 is the same as in FIG. 28, so that the locking jaws 206 and 207 cause no significant resistance to the axial motion of the needle 211, yet continue to provide radial support to it. Thus the withdrawal motion of the needle 211 can continue beyond the critical configuration of FIG. 24, ensuring that sensing ball 205 is released into its cavity 231 to block the re-emergence of the needle point, before the locking jaws 206 and 207 are activated.

When the plunger 203 moves to the position of FIG. 30, it releases latching ball 208 from the confinement of FIGS. 28 and 29, allowing locking jaws 206 and 207 to be driven by spring 204 into the confinement of tapered bore 225 in guard base 201. This causes the jaws 206 and 207 to grip the needle shaft 211. The angle of taper of bore 225 is critically selected with respect to the coefficients of friction between the jaws 206 and 207 and needle shaft 211 and between the jaws and bore 225, such that the axial component of frictional grip between the jaws and the needle shaft is always greater than the externally-applied axial force on the needle, which develops this gripping force. Thus the needle cannot be withdrawn from the needle guard, as the gripping force of the jaws on the needle increases with withdrawal force until material failure occurs. Re-emergence of the needle is resisted to a much lesser degree by the locking jaws 206 and 207, but such re-emergence is blocked by the sensing ball 205 which now blocks the exit path of the needle 211 from the guard.

The self-locking action of the jaws in the direction of withdrawal of the needle from the guard is independent of the axial force on the jaws of spring 204, and the latter acts only as the initiator of the locking action, by moving the jaws onto the confinement of tapered bore 225. Once in this position application of further withdrawal force on the needle 211 enhances the locking effect of the jaws 206 and 207 as they are drawn deeper into the narrowing cavity of the tapered bore 225.

The rotational component of the coefficient of friction between locking jaws 206 and 207 and bore 225 is significantly less than the rotational component of the coefficient of friction between the locking jaws and needle shaft 211. This maintains the rotational grip between the locking jaws and the needle shaft if the latter is rotated with respect to the needle guard, with relative rotation occurring between the locking jaws and bore 225.

The locking jaws 206 and 207 are shown in enlarged views FIGS. 31 to 36. The two jaws are identical, each having a substantially rectangular lug 234 extending from its diametral place on one side of its central axis, which engages a corresponding substantially rectangular recess 235 in the opposite jaw when the two are placed together on a common diametral place. The resulting engagement of each lug and recess prevents relative axial reaction of the two jaws. This allows the use of a single latching ball 208, as described above, holding the two jaws as an axially-coupled pair in the unlocked position.

The tapered outer surface 232, FIG. 31, is polished to reduce the coefficient of friction between the jaw and the bore 225 of the guard body 201.

Figure 36:
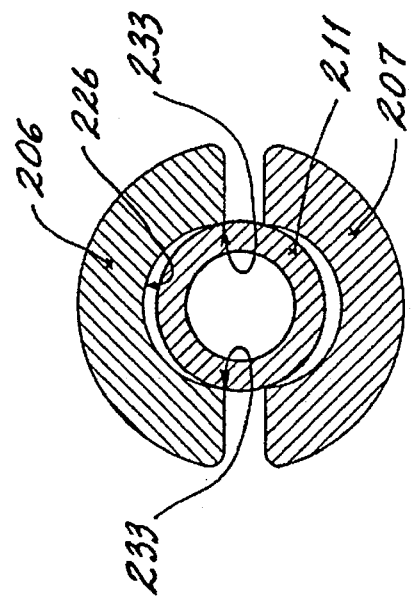
FIG. 36 is an end view cross-section of the jaw element of FIG. 30 as it embraces a needle.

The internal bore 226, FIG. 36, is provided with a relatively coarse surface finish, and is furthermore of a slightly smaller diameter than that of the needle shaft 211. This produces contact with needle shaft 211 along axial lines of concentrated pressure 233, as shown in FIG. 36. This causes the exclusion of any bodily fluids which may be on the surface of the needle, and provides a high frictional grip both axially and rotationally.

This last embodiment demonstrates the use of a narrowing-cavity or chuck-action clamping system, in combination with a sensing ball trigger mechanism. A second latching ball is also employed to maintain the guard in its cocked condition. The major components in this embodiment may be readily manufactured by injection molding without onerous tolerance requirements, and this design has the capacity of having one size fit a range of needle diameters.

Figures 37, 38:
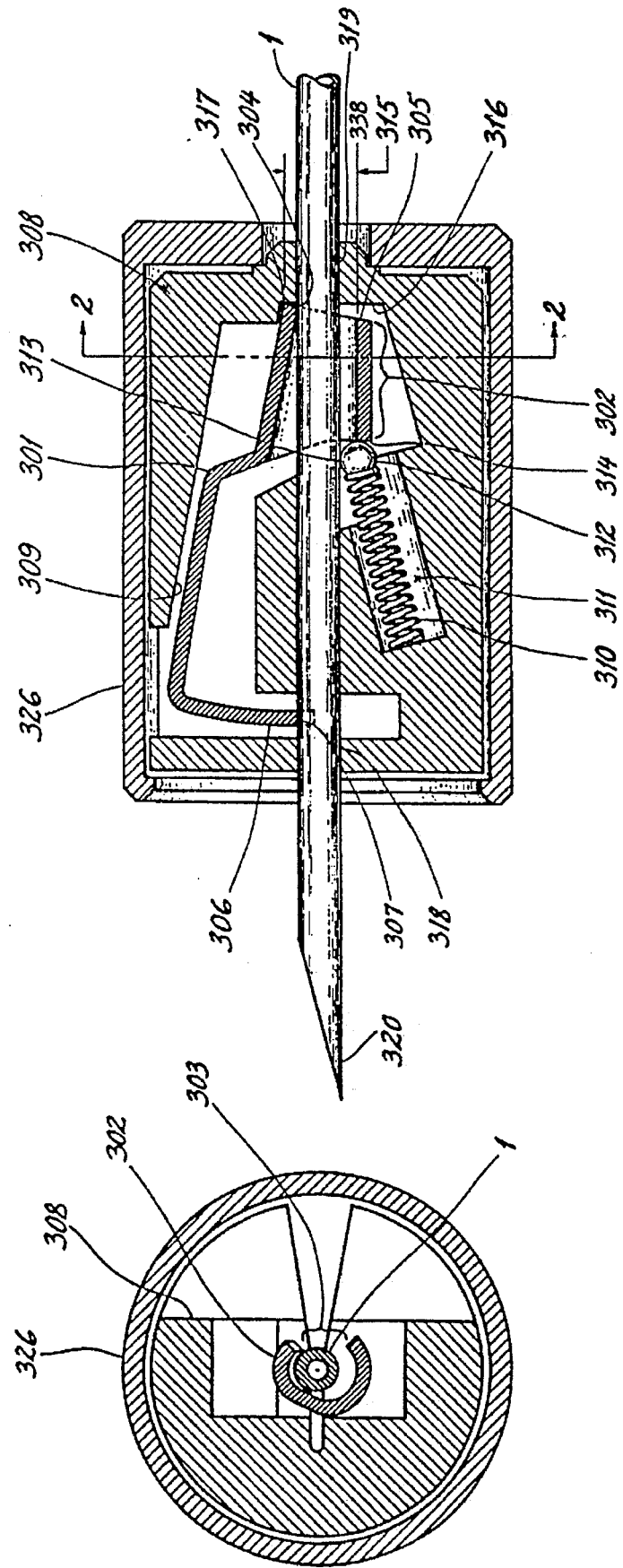
FIG. 37 is a longitudinal section of the "canting-funnel" needle guard device in its unlocked state, prior to use of the needle.
FIG. 38 is a cross-sectional view of FIG. 37.

A further "ball-in-funnel" variant of embodiments of the invention is shown in FIG. 37, which is a longitudinal section of the device. Here the locking means comprises a locking arm 301, right-hand portion 302 of which is in the form of a conical tube or funnel, of generally pear-shaped cross section, more particularly shown in FIGS. 43 to 48. This funnel loosely encloses needle 1, as shown in FIG. 38, except for a slot 303 in one side, which allows the lateral insertion of needle 1 during assembly. Locking arm 301 is furnished with a substantially rectangular extension from the large end of the funnel 302, bent in the general shape of a sickle to form a sensing end 306.

In the needle guard's unlocked state as shown in FIG. 37, arm 301 is canted toward the top of the assembly, pivoting about its point of contact 317 between the small end 305 of the funnel and needle guard body 308. The positioning of needle 1 in funnel 302 is shown in cross-section FIG. 38.

As shown in FIG. 37, in the absence of other forces on arm 301, the left end of the latter is held in this position by its sensing end 306 pressing against needle 1 at point 307, preventing its movement downward. Notch 365, more clearly shown in FIG. 47, prevents lateral movement of end 306 on needle 1.

Significant upward movement of this end of arm 301 is prevented by its near-contact with needle guard body 308 at surface 309. Similarly, right end 305 of arm 301 is confined between needle 1 and body 308 in the region of contact point 317.

Helical compression spring 310 is contained in a largely compressed state within cavity 311 in body 308, cavity 311 being shown somewhat simplified for clarity spring 310 exerts force with its right end against a locking ball 312 so as to direct it to the right, bringing the top of the ball against needle 1 at point 313, and its right side against edge 314 of the large end of funnel 302 on locking arm 301.

The angle of the face of funnel edge 314 with respect to the needle axis is such as to re-direct the spring force to the right, along a line 338 through the centre of ball 312, and at a perpendicular distance 315 from pivot point 317. This forms a turning moment, tending to rotate locking arm 301 in a counter-clockwise direction about pivot point 317. This motion is blocked by contact of sensing end 306 with needle 1 at point 307, as already described. The rightward direction of the spring force against arm 301 also maintains its small end 305 in contact with inner face 316 of body 308 at point 317.

In this unlocked state of the needle guard, axial motion of needle 1 through the guard is impeded only by the small frictional forces occurring from contact of the needle with locking arm 301 at points 304 and 307, with locking ball 312 at point 313, and with body 308 at needle passages 318 and 319.

If needle 1 is drawn to the right through the needle guard until its point 320 is in the position shown in FIG. 39 contact between sensing end 306 and the needle is lost, allowing locking arm 301 to rotate counter-clockwise under the urging of spring-driven ball 312, pressing against edge 314 of funnel 302, as already described for FIG. 37.

When locking arm 301 has rotated to almost the position shown in FIG. 39, ball 312 is able to move past edge 314 of the funnel and to enter the converging space 321 between the bottom of needle 1 and the lower inner surface 322 of funnel 302. Travel of ball 312 is halted when it becomes wedged between contact point 323 with needle 1 and contact point 324 with lower inner surface 322 of funnel 302. The upward pressure from ball 312 on needle 1 at point 323 presses the needle into contact with points 323 and 324, caused by the force of spring 310, are moderate only, sufficient to ensure rolling of the ball through friction if the needle is moved axially.

If an attempt is made to remove needle 1 by drawing it further to the right relative to the needle guard, locking ball 312 will roll to the right with the needle, entering more deeply into converging cavity 321, and increasing the pressure at contact points 323 and 324. By setting the slope angle 325 of funnel 302 equal to or less than a critical value $A_{crit}$, the resulting leftward frictional forces developed on the needle by this rolling and wedging action will always equal the rightward force applied to needle 1 in attempting to remove it from the needle guard.

If the coefficient of friction between the needle and funnel surface and between needle and ball is denoted as F, then it can be shown that the critical value of angle 325 is:

$$A_{crit} = \sin^{-1}\{2F/(F^2+1)\}$$

and is typically about twelve degrees. Provided that angle 325 is less than this value, the maximum attainable axial frictional force to the left on the needle, generated by the external pull to the right, will always exceed the pull, so that the needle cannot be removed from the needle guard, unless material failure or deformation occurs.

The rightward pull on needle 1 is transferred through friction to funnel 302, and thence to body 308 by engagement of the small end 305 of the funnel with inner face 316 of the body.

If, after locking as in FIG. 39, needle 1 is pushed axially to the left with respect to the needle guard, ball 312 will tend to roll with the needle out of the confinement of funnel 302, releasing the wedging action of the latter on the ball. This will release the grip of the needle guard on the needle, allowing the latter to slide past ball 312 and move towards re-emergence of needle point 320 from the guard. However, sensing end 306 prevents this by solidly obstructing the path of the needle point, and is maintained in this position by ball 312 being held in space 321 by the force of spring 310. Leftward force of needle point 320 against lever sensing end 306 is transmitted to body 308 by contact of end 306 with inside surface 362 of the end of body 308.

The grip between funnel 302 and needle 1 is by friction, without significant penetration of the needle surface by ball 312. Thus, any rotation of the needle about its axis relative to the funnel while an external pull is applied to the needle will result in some axial slippage of this frictional grip. This would allow the needle to be deliberately removed from the needle guard, by persistent rotating or twisting back and forth of the needle in the guard.

To prevent this, a rotatable outer shell 326 is preferably, though optionally, provided, fitting loosely about body 308, as shown in FIG. 39. Rightward axial thrust against the outer shell by body 308 is transmitted by spigot 327 on its right end, which fits into opening 360 on inner end face 328 of outer shell 326. Because of the small diameter of the contact surface between spigot 327 and outer shell 326, the rotation resistance to turning of body 308 within the shell is small, and less than that between needle 1 and funnel 302 when locked. This provides rotational isolation of the needle guard from external handling.

Body 308 is typically pressed axially into the open left end of shell 326 during assembly, and retained within the shell by snap lips 329 formed on the open end of the outer shell, and which engage left end face 330 of body 308, as shown in FIG. 39. Because needle opening 360 in closed end 361 of outer shell 326 is significantly larger than the diameter of needle 1, the outer shell may be safely passed over the end of the needle during assembly.

Alternatively, outer shell 326 may be made in two or more longitudinally-divided sections, optionally hinged at their meeting edges, and designed to close about the needle in book-fashion, with integral or separate snap means provided to hold the sections in their closed state. Alternatively, the sections may be bonded together after assembly, using such means as adhesive, ultra-sonic welding, or the like. Using such an outer shell, all parts of the needle guard may be assembled to the needle from the side.

FIG. 40 is a cross-sectional view of the needle, ball and funnel in the locked state of FIG. 39, with other components omitted for clarity. The wedging action of needle 1A and ball 312A in funnel 302 is transmitted to the funnel as outwardly-directed forces along axial contact line 331 and at point 324 respectively. Because these forces are typically about ten times the external pull which may be applied to needle 1 in an attempt to remove it forcibly from the locked needle guard, thickness 332 of the funnel must be sufficient to provide adequate strength against spreading apart of the funnel under such conditions.

FIG. 41 is the same cross-section of funnel 302 as in FIG. 40, but with needle 1A replaced by needle 1B of smaller diameter than that of FIG. 4. Ball 312A has been replaced by ball 312B of correspondingly larger diameter, so that their total height 333 is the same as in FIG. 40. This allows the same locking arm 301 to be used for a number of different needle diameters, simply by using different diameters of locking ball 312. Furthermore, a given diameter of locking ball may accommodate more than one needle diameter, since minor differences in dimension 333 can be accommodated simply by ball 312 locking at different axial positions in funnel 302.

FIG. 42 is a partial longitudinal section similar to FIG. 1, but with large needle size 1A and its small locking ball 312A superimposed on smaller needle size 1B and its larger locking ball 312B. This illustrates that in the unlocked state as described above for FIG. 37, essentially the same geometry of needle, ball, and funnel occurs for two significantly different needle sizes. This establishes for both configurations the counter-clockwise turning moment on arm 301 required to maintain sensing end 306 in contact with needle 1 in this unlocked state, as already described.

FIG. 49 shows body 308 in isolation as a side view, rather than in section as in FIGS. 37 and 39. This gives a more detailed view of needle passages 318 and 319 in the left and right ends, as well as needle passage 334 and spring recess 311 in the central portion 335 of the body.

As more clearly seen in left end view FIG. 14, needle passage 318 is largely circular in cross-section, but is pierced radially on one side by a wedge-shaped slot 336, and on the other side by a generally rectangular slot 337, which is an extension of slot 336. The same general configuration is used in needle passages 319 and 334.

Slot 336, serves as an entry for the lateral insertion of needle 1, while slot 337, which extends axially partway into the bulk of body 308 over the axial length of the latter, provides some hinge-like flexibility to that portion of the body to allow the needle passageways to open slightly. This permits needle 1 to snap past constriction 339 during assembly of the needle guard, after which the constriction largely closes behind the needle to confine it loosely in central circular portion 318. To aid in this needle-insertion process, wedge-shaped portion 336 may be expanded temporarily by a generally wedge-shaped insertion bar 340, forming part of the assembly machine, and which also provides the lateral insertion force 341 to needle 1 during insertion of the latter, as shown in FIG. 50.

This lateral insertion allows the needle to be installed in body 308 without having to pass the latter over either end of the needle, thus preventing damage to the pristinely sharp needle point 320. Similarly, slot 303 in locking arm funnel 302, FIGS. 43 and 48, allows the needle to be placed in the funnel entirely from the side, without jeopardy to the needle point.

FIG. 51 is a top view of body 308 in isolation, with a broken section, showing principally the placement of spring cavity 311. This cavity is more clearly seen in partial section FIG. 52, made along the axis of cavity 311 by oblique section plane 16—16 shown in FIG. 49. Spring 310, ball 312 and lever 301 have been added to FIG. 52 to show their relationship to one another as a top view in the unlocked state.

Figure 53:
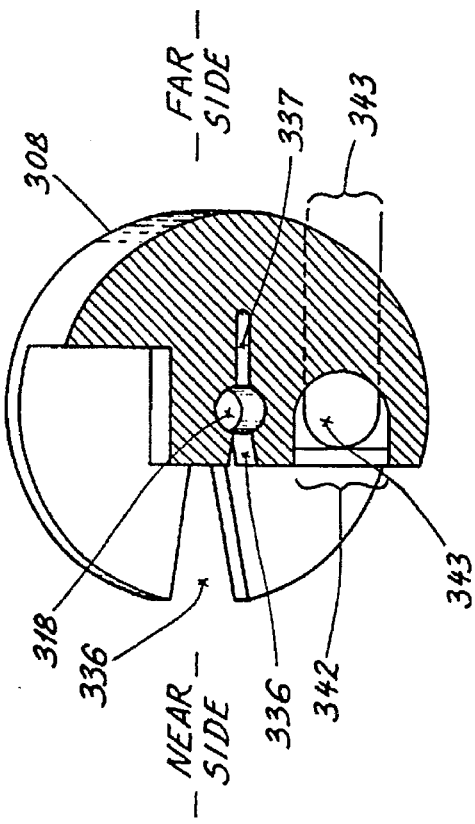
FIG. 53 is an oblique cross-section of FIG. 49 showing the needle cavity and spring cavity.

FIG. 53 is a section made transversely to the axis of cavity 311 by oblique section plane 17—17 in FIG. 49. The spring 310 and ball 312 have been omitted for clarity. As can be seen here, central portion 342 of spring cavity 311 may be cored from the near side during molding.

Referring to FIG. 49, the remainder of cavity 311 comprises lower left portion 343 and upper right portion 344, both cored from the far side of the body during molding, as shown by broken lines in FIG. 51. Portions 342 and 343 are more clearly seen in FIG. 53. The closed ends of all three cavity portions consist of semi-circular surfaces commonly centred on the axis of spring cavity 311, and overlapping one another alternately to form a continuous passage for spring 310. This overlapping is also shown by the broken lines in FIG. 51.

Figure 52:
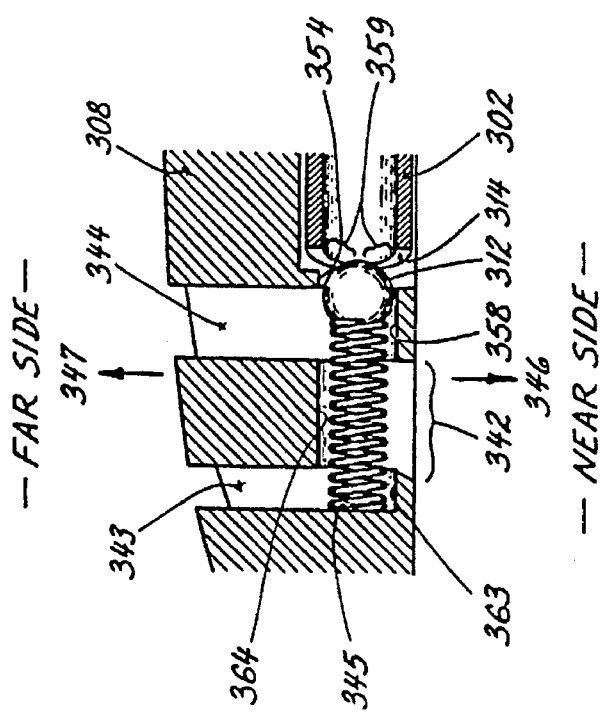
FIG. 52 is a partial oblique longitudinal section of FIG. 49, with locking ball, spring, and locking arm shown in the unlocked state.

As shown in FIG. 52, cavity 343 forms a closed left end surface 345 for the spring passage, providing a seat for the fixed end of spring 310. The closed semi-circular near-side end surfaces 363 and 358 of cavities 343 and 344 restrain spring 310 from moving in direction 346. Similarly the semi-circular far-side end surface 364 of cavity 342 restrains the spring from moving in direction 347. Because the spring is smaller in diameter than the spring passage enclosing it, this restraint is radially loose.

Figure 55:
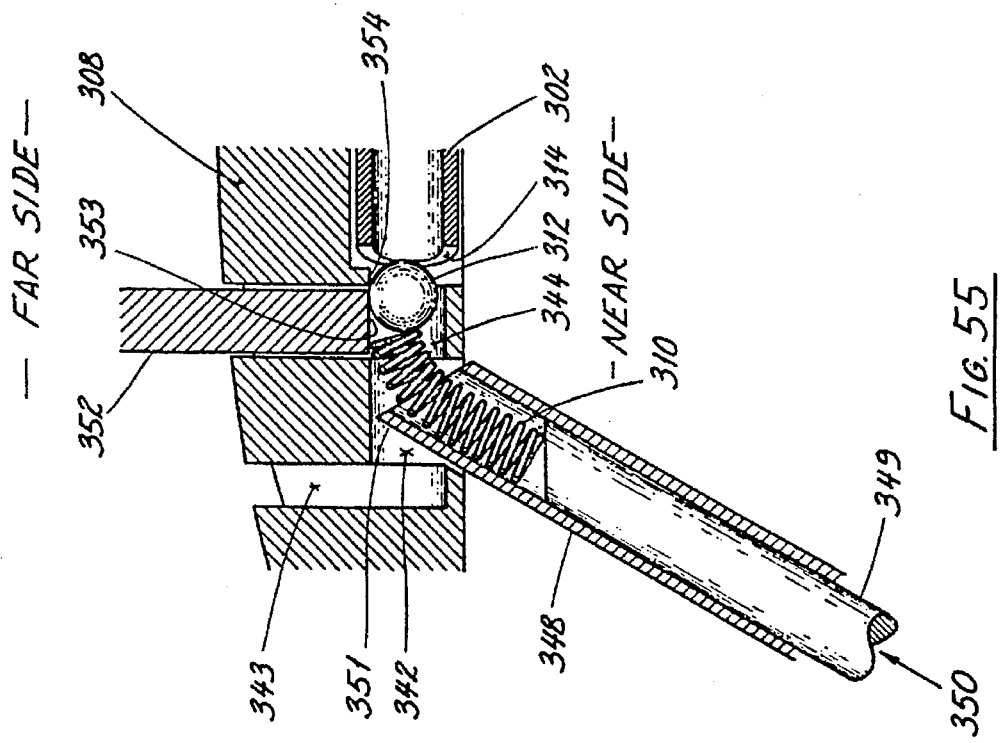
FIG. 55 is the partial oblique section of FIG. 52, showing the second stage of the installation of the locking ball and its spring.
Figure 54:
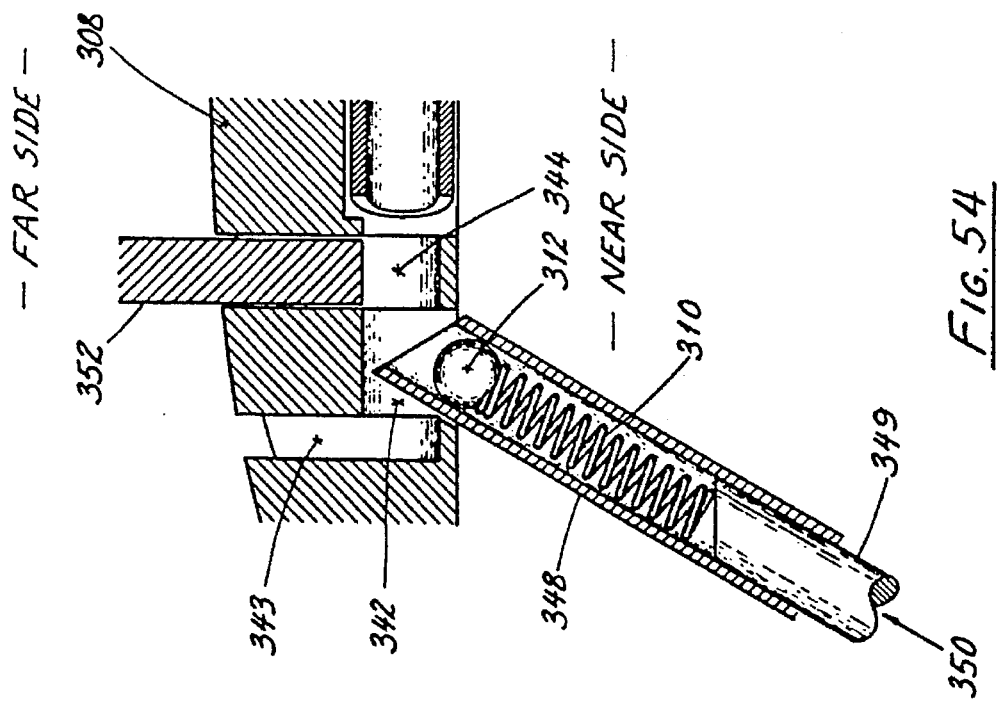
FIG. 54 is the partial oblique section of FIG. 52, showing the first stage of the installation of the locking ball and its spring.
Figure 56:
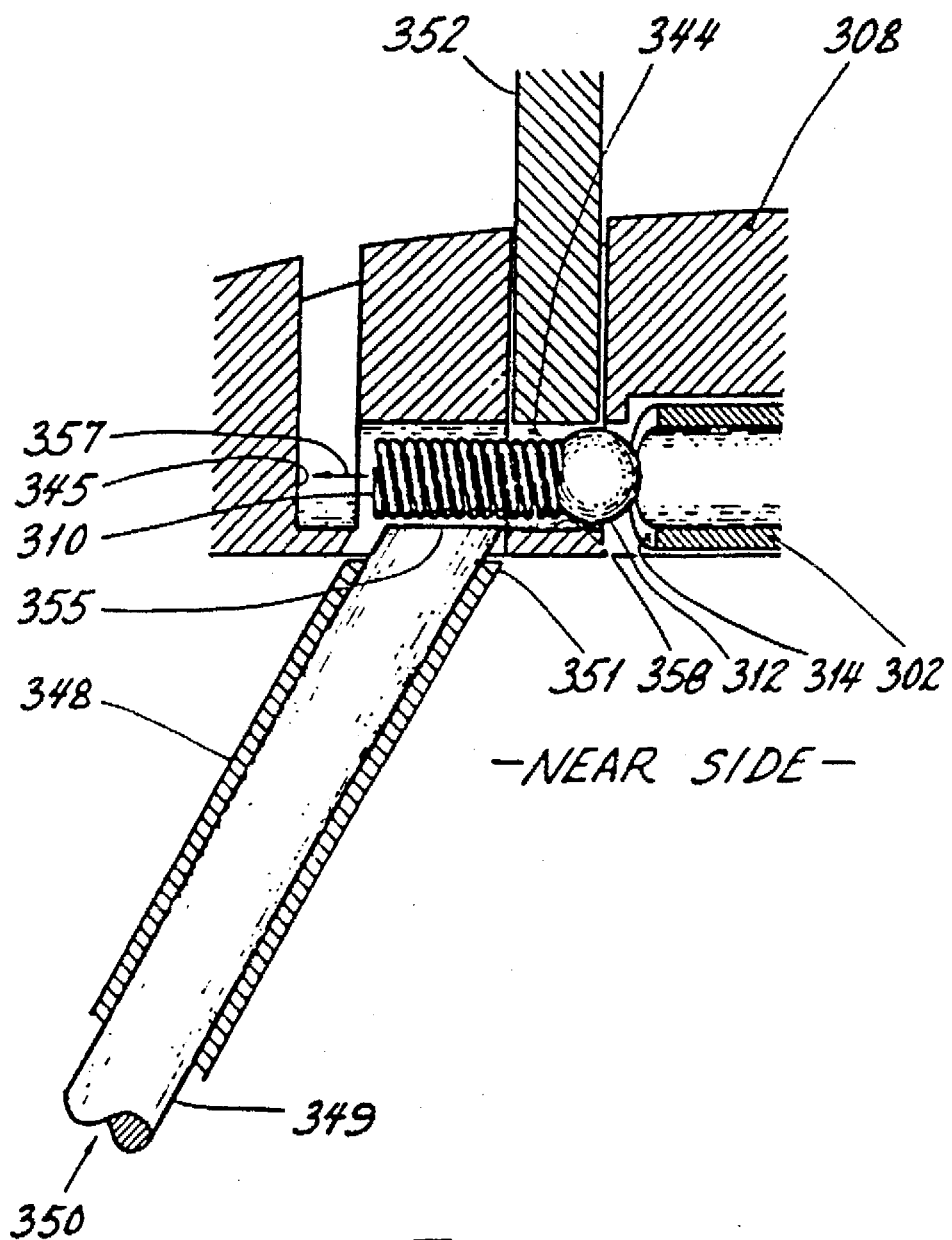
FIG. 56 is the partial oblique section of FIG. 52, showing the third stage of the installation of the locking ball and its spring.

FIGS. 54, 55, and 56 are sections similar to FIG. 52, and depict an example of how the configuration of spring cavity 311 is utilized during that part of the assembly stage involving installation of spring 310 and ball 312. This stage begins with needle 1 and looking arm 301 already in place in body 308, and arm 301 placed in the upwardly-canted, unlocked position shown in FIG. 37. In FIGS. 54, 55, and 56 the needle is not shown, and only the lower portion of funnel 302 of arm 301 is visible, in section.

In FIG. 54, insertion tube 348, which forms part of the needle guard assembly machine, has been obliquely inserted into the open near-side of cavity 342. Locking ball 312 and spring 310 are shown being delivered in sequence through tube 348 by plunger 349, moving in direction 350.

In FIG. 55, ball 312 has entered and passed through cavity 342. Angled tip 351 of insertion tube 348 blocks any motion to the left by the ball, which has been diverted to the right under the urging of spring 310, pushed in turn by insertion plunger 349 in direction 350. This diversion of the ball is aided by the insertion of guide core 352 partway into cavity 344, forming a temporary wall face 353 as a continuation of ball support face 354 on body 308. Ball 312 has crossed cavity 344, to rest against edge 314 of funnel 302. The motion of plunger 349 continues, compressing spring 310 against ball 312.

In FIG. 56 insertion tube 348 has been partially withdrawn from cavity 342 independently of plunger 349, and rotated about its axis by a half-turn, so that its angle tip 351 now lies parallel to the needle axis. Plunger 349 has advanced in direction 350 until its angled tip 355 is level with end surface 358 of cavity 344. This allows compressed spring 310 to expand axially, with its left end sliding free in direction 357 as shown, until it seats itself against surface 345, as shown in FIG. 52. Insertion tube 348 and plunger 349, together with guide core 352, are then retracted from body 308, completing this stage of assembly.

With locking ball 312 in position in the unlocked state as shown in FIG. 52, it is restrained from moving in direction 346 by cavity end surface 358, and in direction 347 by support surface 354. During the locking sequence, as edge 314 of funnel 302 begins to drop from the position shown in FIG. 37, ball 312 emerges from cavity 344 and away from the support of surfaces 358 and 354. During this transition, curved sides 359 of funnel 302, shown in FIG. 52, provide support in directions 346 and 347 by partially embracing ball 312 until it fully enters the funnel and is seated in its curved lower surface 322, as shown in FIGS. 39, 40, and 41.

All of the principal parts of the device may be made of any suitable material, such as of injection moulded plastic, eg. Nylon, or of corrosion-resistant metal such as stainless steel, according to such considerations as convenience of manufacture, cost and other factors relevant to medical devices.

Throughout the foregoing disclosure a hollow hypodermic needle has been depicted. The needle need not, however, be hollow. The protective guard contemplated by this invention is equally applicable to solid needles, such as might be used for smallpox inoculations or as solid cores for wire catheters.

CONCLUSION

The foregoing has constituted a description of specific embodiments showing how the invention may be applied and put into use. These embodiments are only exemplary. The invention in its broadest, and more specific aspects, is further described and defined in the claims which now follow.

These claims, and the language used therein, are to be understood in terms of the variants of the invention which have been described. They are not to be restricted to such variants, but are to be read as covering the full scope of the invention as is implicit within the invention and the disclosure that has been provided herein.

The embodiments of the invention in which an exclusive property are claimed as follows:

1. A needle tip protecting device for covering the tip of a needle comprising protecting means having engagement means for automatically, non-removably, directly engaging the outer surface of needle with said protecting means when said protecting means is moved from a position on said needle spaced from said tip, to a position where said protecting means encloses said tip, said engagement means comprising:
  (a) locking means adapted to lockingly engage with said needle and thereby restrain axial displacement of said protecting means with respect to said needle in the direction proceeding towards the tip of said needle, when said protecting means encloses said tip; and
  (b) means to prevent re-emergence of said tip from said guard body upon attempted movement of said protecting means in the opposing axial direction wherein the locking means comprises:
  (i) a jamming surface contained within said protecting means and obliquely aligned with said needle to provide a narrowing opening therebetween; and
  (ii) jamming means contained within said protecting means and biased by spring means to move into the narrowing opening and lockingly engage said needle when said protecting means is positioned so as to envelop the tip of said needle.

2. A needle tip protecting device as in claim 1 further comprising:
  (a) retention means for releaseably suspending the actuation of said locking means and release of the jamming means to enter the narrowing opening; and
  (b) trigger means for sensing the presence or absence of the needle tip within the protecting means and releasing the retention means when the needle tip is withdrawn within the protecting device.

3. A needle tip protecting device as in claim 1 in comprising:
  (a) a body provided with a passage therethrough for enveloping a needle inserted therein, said body carrying each of said jamming surface, jamming means and spring means, with said jamming means being positioned to advance into said narrowing opening;

and further comprising:
  (b) latch means positioned to releaseably restrain said jamming means from being advanced into said opening; and
  (c) trigger means, positioned to release said jamming means when the tip of said needle is withdrawn into said guard body.

4. A needle tip protecting device as in claim 3 wherein the jamming surface is formed as an interior surface of the body.

5. A needle tip protecting device as in claim 1 comprising:
  (a) a body with a needle entry hole therethrough for slideably carrying the shaft of a needle axially therein, wherein said jamming surface is carried by a canting funnel contained within said body for pivotable rotation about a pivot point on said body, and further comprising:

(b) alignment means to maintain said canting funnel and said needle in a first position of orientation to said needle while the needle tip is outside of said protecting means; and (c) canting means to cant said canting funnel to a second position of orientation to said needle, providing said narrowing opening and permitting the jamming means to enter therein and effect locking engagement with said needle when said tip enters within said protection means.

6. A needle protecting device as in claim 5 wherein said canting means comprises a spring means with two ends, the first end thereof being in contact with said body and the second end thereof being connected to said canting funnel to bias said funnel to rotate about said pivot point.

7. A needle tip protecting device as in claim 5 wherein said alignment means comprises a lever arm with first and second ends contained within said body, the first end of said lever arm being attached to said funnel, and the second end of said lever arm being in contact with said needle, said lever arm being positioned and aligned to prevent canting of said funnel only so long as said needle tip is in contact with the second end of the lever arm.

8. A needle tip protecting device as in claim 1 comprising a sensing means for detecting the presence and absence of the needle tip within the protecting means and for activating engagement of said protecting means with said needle when said tip is drawn Within said protecting means.

9. A needle tip protecting device as in claim 8 wherein said sensing means comprises a pivoting arm with a free sensing end, said arm being biased to rotate about a pivot point in a direction that tends to bring said sensing end into the path of said needle through said device, said arm being restrained from rotation by the presence of said needle in contact with said sensing end.

10. A needle tip protecting device as in claim 1 comprising an outer, substantially cylindrical shell, rotationally isolated from said protecting means so as to prevent said protecting means from being disengaged from said needle by the application of an external rotational force, after engagement with said needle has been effected.

11. The needle tip protecting device as in claim 1 in combination with a needle and a syringe.

12. The needle tip protecting device of claim 5 in combination with an intravenous catheter assembly comprising an intravascular catheter with a base, an insertion needle, coupling means mounted on said base for releasably coupling with a needle tip protecting device wherein said needle tip protective device:

(a) is coupled to and initially retained with said base of said intravenous catheter, with said insertion needle passing therethrough;

(b) remains attached to said catheter base during withdrawal of said needle from said catheter, until the tip of said needle enters said needle protective device and is non-removably engaged therein; and (c) thereafter may be detached from said catheter base by further axial withdrawal of said insertion needle.

* * * * *